(12) United States Patent
Young et al.

(10) Patent No.: US 7,485,300 B2
(45) Date of Patent: Feb. 3, 2009

(54) CANCEROUS DISEASE MODIFYING ANTIBODIES

(75) Inventors: David S. F. Young, Toronto (CA); Helen P. Findlay, Toronto (CA); Susan E. Hahn, Toronto (CA); Lisa M. Cechetto, Seoul (KR); Fortunata McConkey, Shelburne (CA); Daad Sayegh, Mississauga (CA)

(73) Assignee: Arius Research Inc., Toronto, Ontario (CA)

( * ) Notice: Subject to any disclaimer, the term of this patent is extended or adjusted under 35 U.S.C. 154(b) by 115 days.

(21) Appl. No.: 11/709,457

(22) Filed: Feb. 22, 2007

(65) Prior Publication Data

US 2007/0202042 A1 Aug. 30, 2007

Related U.S. Application Data

(60) Provisional application No. 60/776,262, filed on Feb. 24, 2006.

(51) Int. Cl.
*A61K 39/00* (2006.01)
(52) U.S. Cl. ............... 424/133.1; 530/387.1; 424/178.1
(58) Field of Classification Search ................. None
See application file for complete search history.

(56) References Cited

U.S. PATENT DOCUMENTS

| | | | |
|---|---|---|---|
| 4,861,581 A | 8/1989 | Epstein et al. | |
| 5,171,665 A | 12/1992 | Hellstrom et al. | |
| 5,484,596 A | 1/1996 | Hanna, Jr. et al. | |
| 5,693,763 A | 12/1997 | Codington et al. | |
| 5,750,102 A | 5/1998 | Eisenbach et al. | |
| 5,780,033 A | 7/1998 | Torchilin et al. | |
| 5,783,186 A | 7/1998 | Arakawa et al. | |
| 5,849,876 A | 12/1998 | Linsley et al. | |
| 5,869,045 A | 2/1999 | Hellstrom et al. | |
| 5,869,268 A | 2/1999 | Kudo et al. | |

OTHER PUBLICATIONS

Daad et al., "97th American Association for Cancer Research Annual Meeting", Apr. 1-5, 2006, Toronto, Canada, Abstract 637.
Green et al., "Disruption of Cell-Cell Adhesion Enhances Antibody-Dependent Cellular Cytotoxicity: Implications for Antibody-Based Therapeutics of Cancer", Cancer Research (2002), vol. 62, pp. 6891-6900.
Kohler et al, "Continuous Cultures of Fused Cells Secreting Antibody of Predefined Specificity", Nature (Aug. 1975), vol. 256, pp. 495-497.
Liu et al., "Eradication of Large Colon Tumor Xenografts by Targeted Delivery of Maytansinoids", Proceedings of the National Academy of Sciences of the U.S.A. (1996), vol. 93, pp. 8618-8623.
Mount et al., "Chimeric (Mouse/Human) Anti-Colon Cancer Antibody c30.6 Inhibits the Growth of Human Colorectal Cancer Xenografts in scid/scid Mice", Cancer Research (1994), vol. 54, pp. 6160-6166.

*Primary Examiner*—Larry R. Helms
*Assistant Examiner*—Meera Natarajan
(74) *Attorney, Agent, or Firm*—McHale & Slavin, P.A.

(57) ABSTRACT

The present invention relates to a method for producing cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, cytokines, interferons, target or reporter moieties and hematogenous cells.

36 Claims, 11 Drawing Sheets
(3 of 11 Drawing Sheet(s) Filed in Color)

FIGURE 1

| | Isotype ELISA Fold | | Percentage Cytotoxicity | | | | | | | | | Binding | | | | |
|---|---|---|---|---|---|---|---|---|---|---|---|---|---|---|---|---|
| | | | MB-231 | | OVCAR-3 | | SW1116 | | Lovo | | CCD-27sk | | MB-231 | OVCAR-3 | SW1116 | Lovo | CCD-27sk |
| | IgG | IgM | Average | CV | Average | CV | Average | CV | Average | CV | Average | CV | fold | fold | fold | fold | fold |
| AR58A314.1 | 3.5 | 0.6 | 7 | 5 | 13 | 10 | 13 | 7 | 12 | 3 | -8 | 10 | 1.0 | 1.1 | 1.3 | 1.3 | 1.0 |
| Controls Cyclohexamide | | | 45 | 30 | 30 | 19 | 20 | 18 | 46 | 14 | 22 | 18 | | | | | |
| NaN₃ | | | 31 | 45 | 55 | 10 | | | -3 | -382 | -30 | -35 | | | | | |
| c225 | | | | | | | 32 | 15 | | | | | | | | | |

FIGURE 2

| | Cell Line | Colon | | | Lung | Pancreatic | | Breast | Prostate | Ovarian | Normals | |
|---|---|---|---|---|---|---|---|---|---|---|---|---|
| | | DLD-1 | Lovo | SW620 | SW1116 | A549 | AsPC-1 | BxPC-3 | MDA-MB-231 | PC-3 | OVCAR-3 | CCD-27sk | Hs888.Lu |
| | AR58A314.1 | 1.8 | 2.0 | 8.5 | 2.1 | 1.4 | 1.3 | 0.8 | 1.1 | 1.5 | 1.6 | 1.1 | 1.1 |
| Positive Control | anti-EGFR | 26.2 | 9.7 | 1.7 | 7.5 | 25.2 | 22.1 | 15.5 | 24.5 | 21.4 | 30.0 | 5.1 | 12.0 |

FIGURE 8

| Localization | Organ | AR58A314.1 | | Anti-actin | | Isotype Control | |
|---|---|---|---|---|---|---|---|
| | | Section Score | Tissue Specificity | Section Score | Tissue Specificity | Section Score | Tissue Specificity |
| A 1a | Prostate | - | - | - | Tumor cells | - | - |
| A 1b | Prostate | - | - | ++ | Tumor stroma | - | - |
| | | | | | Tumor cells | | |
| A 1c | Prostate | - | - | + | Tumor stroma | NR | NR |
| | | | | | Tumor cells | | |
| A 1d | Prostate | - | - | ++ | Tumor stroma | - | - |
| A 1e | Prostate normal | - | - | ++ | Tumor stroma | - | - |
| A 2a | Lung | - | - | - | Stroma | - | - |
| A 2b | Lung | - | - | - | - | - | - |
| A 2c | Lung | +/- | Tumor cells | SF | - | - | - |
| A 2d | Lung | +/- | Tumor cells | SF | - | - | - |
| A 2e | Lung normal | - | - | - | SMF of blood vessels | - | - |
| | | | | | tumor cells | | |
| A 3a | Colon | - | - | ++ | Tumor stroma | - | - |
| A 3b | Colon | - | - | - | - | - | - |
| A 3c | Colon | +/- | Tumor cells | SF | - | - | - |
| A 3d | Colon | - | - | - | - | - | - |
| A 3e | Colon normal * | - | - | - | SMF of blood vessels | - | - |
| A 4a | Breast | - | - | - | - | - | - |
| A 4b | Breast | - | - | - | - | - | - |
| A 4c | Breast | - | - | - | - | - | - |
| A 4d | Breast | - | - | - | - | - | - |
| A 5a | Breast normal ** | - | - | - | SMF of blood vessels | - | - |

Legend: Negative staining: -; Equivocal staining: +/-; Weak staining: +; Moderate staining: ++; Strong staining: +++;
Sporadic focal staining: SF; Not representative: NR; Connection tissue only (no mucosa): *; Stroma only (no ducts or ductules): **.

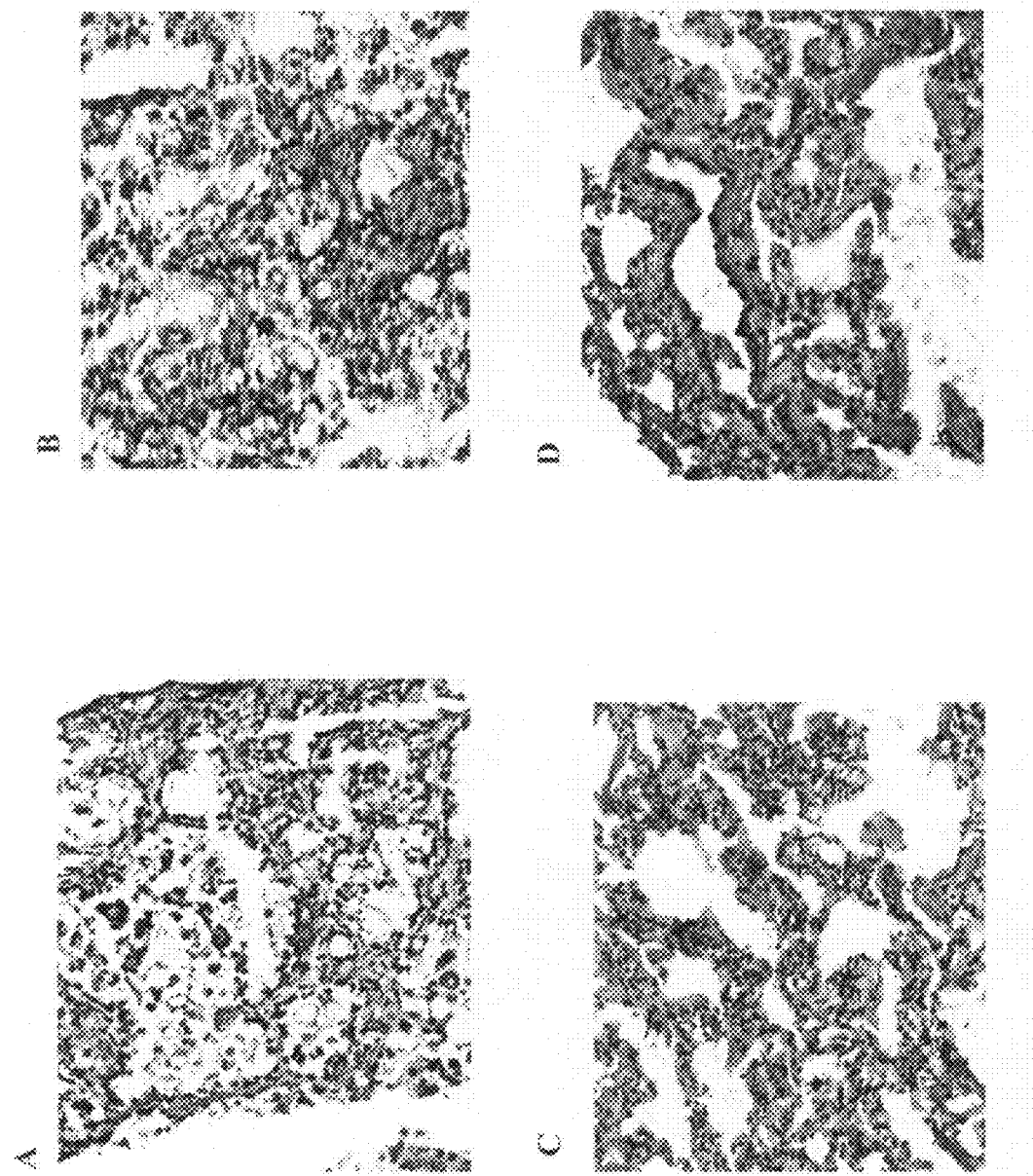

FIGURE 10

| Data Sheet | | | | IHC | | | | |
| --- | --- | --- | --- | --- | --- | --- | --- | --- |
| | | | | AR58A314.1 | IgG negative | | Anti-Actin | |
| Tissue Type | Age | Sex | Diagnosis | Section scroe | Section scroe | Section scroe | Tissue specificity |
| Adrenal | 76 | F | Normal | Bg | Bg | Bg | Bg |
| Ovary | 37 | F | Normal | - | - | +++ | SMF of blood vessels and stroma |
| Pancreas | 62 | M | Normal | - | - | ++ | SMF of blood vessels |
| Thyroid | 62 | M | Normal | - | - | ++ | SMF of blood vessels |
| Brain, Cerebrum | 70 | F | Normal | - | - | - | - |
| Brain, Cerebellum | 26 | M | Normal | - | - | +++ | SMF of blood vessels |
| Lung | 83 | F | Normal | - | - | +++ | SMF of blood vessels |
| Spleen | 24 | M | Normal | - | -* | +++ | SMF |
| Uterus | 47 | F | Normal | - | - | ++ | SMF of blood vessels |
| Cervix | 49 | F | Normal | - | -** | +++ | Glandular epithelium and stroma |
| Breast | 78 | F | Normal | Bg | Bg | Bg | Bg |
| Placenta | 27 | F | Normal | - | - | +++ | Cardiac muscle fibers |
| Heart | 19 | F | Normal | - | - | ++ | SMF of blood vessels |
| Skin | 21 | F | Normal | - | - | ++ | Skeletal muscle fibers |
| Skeletal Muscle | 26 | M | Normal | Bg | - | +++ | SMF of blood vessels and tubular epithelium |
| Kidney | 62 | M | Normal | - | -* | +++ | SMF |
| Stomach | 22 | M | Normal | Bg | Bg | Bg | Bg |
| Small Intestine | 40 | F | Normal | Bg | Bg | Bg | Bg |
| Liver | 30 | M | Normal | Bg | Bg | Bg | Bg |
| Salivary Gland | 84 | M | Normal | Bg | Bg | Bg | Bg |

* Background of interstial tissue
** Weak background of stroma
Bg: Background
SMF: Smooth muscle fiber

CANCEROUS DISEASE MODIFYING ANTIBODIES

REFERENCE TO RELATED APPLICATIONS

This application claims benefit of the filing date of Provisional Application 60/776,262, filed on Feb. 24, 2006, the contents of which are herein incorporated by reference.

FIELD OF THE INVENTION

This invention relates to the isolation and production of cancerous disease modifying antibodies (CDMAB) and to the use of these CDMAB alone or in combination with one or more CDMAB/chemotherapeutic agents in therapeutic and diagnostic processes. The invention further relates to binding assays which utilize the CDMAB of the instant invention.

BACKGROUND OF THE INVENTION

Monoclonal Antibodies as Cancer Therapy: Each individual who presents with cancer is unique and has a cancer that is as different from other cancers as that person's identity. Despite this, current therapy treats all patients with the same type of cancer, at the same stage, in the same way. At least 30 percent of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells. However, it is now widely recognized that no single monoclonal antibody can serve in all instances of cancer, and that monoclonal antibodies can be deployed, as a class, as targeted cancer treatments. Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-Her2/neu antibody (Herceptin®) in combination with CISPLATIN. In this trial 37 patients were assessed for responses of which about a quarter had a partial response rate and an additional quarter had minor or stable disease progression. The median time to progression among the responders was 8.4 months with median response duration of 5.3 months.

Herceptin® was approved in 1998 for first line use in combination with Taxol®. Clinical study results showed an increase in the median time to disease progression for those who received antibody therapy plus Taxol® (6.9 months) in comparison to the group that received Taxol® alone (3.0 months). There was also a slight increase in median survival; 22 versus 18 months for the Herceptin® plus Taxol® treatment arm versus the Taxol® treatment alone arm. In addition, there was an increase in the number of both complete (8 versus 2 percent) and partial responders (34 versus 15 percent) in the antibody plus Taxol® combination group in comparison to Taxol® alone. However, treatment with Herceptin® and Taxol® led to a higher incidence of cardiotoxicity in comparison to Taxol® treatment alone (13 versus 1 percent respectively). Also, Herceptin® therapy was only effective for patients who over express (as determined through immunohistochemistry (IHC) analysis) the human epidermal growth factor receptor 2 (Her2/neu), a receptor, which currently has no known function or biologically important ligand; approximately 25 percent of patients who have metastatic breast cancer. Therefore, there is still a large unmet need for patients with breast cancer. Even those who can benefit from Herceptin® treatment would still require chemotherapy and consequently would still have to deal with, at least to some degree, the side effects of this kind of treatment.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minor responses among 52 patients in protocols using additional cyclophosphamide. To date, Phase III clinical trials of 17-1A have not demonstrated improved efficacy as adjuvant therapy for stage III colon cancer. The use of a humanized murine monoclonal antibody initially approved for imaging also did not produce tumor regression.

Only recently have there been any positive results from colorectal cancer clinical studies with the use of monoclonal antibodies. In 2004, ERBITUX® was approved for the second line treatment of patients with EGFR-expressing metastatic colorectal cancer who are refractory to irinotecan-based chemotherapy. Results from both a two-arm Phase II clinical study and a single arm study showed that ERBITUX® in combination with irinotecan had a response rate of 23 and 15 percent respectively with a median time to disease progression of 4.1 and 6.5 months respectively. Results from the same two-arm Phase II clinical study and another single arm study showed that treatment with ERBITUX® alone resulted in an 11 and 9 percent response rate respectively with a median time to disease progression of 1.5 and 4.2 months respectively.

Consequently in both Switzerland and the United States, ERBITUX® treatment in combination with irinotecan, and in the United States, ERBITUX® treatment alone, has been approved as a second line treatment of colon cancer patients who have failed first line irinotecan therapy. Therefore, like Herceptin®, treatment in Switzerland is only approved as a combination of monoclonal antibody and chemotherapy. In addition, treatment in both Switzerland and the US is only approved for patients as a second line therapy. Also, in 2004, AVASTIN® was approved for use in combination with intravenous 5-fluorouracil-based chemotherapy as a first line treatment of metastatic colorectal cancer. Phase III clinical study results demonstrated a prolongation in the median survival of patients treated with AVASTIN® plus 5-fluorouracil compared to patients treated with 5-fluourouracil alone (20 months versus 16 months respectively). However, again like Herceptin® and ERBITUX®, treatment is only approved as a combination of monoclonal antibody and chemotherapy.

There also continues to be poor results for lung, brain, ovarian, pancreatic, prostate, and stomach cancer. The most promising recent results for non-small cell lung cancer came from a Phase II clinical trial where treatment involved a monoclonal antibody (SGN-15; dox-BR96, anti-Sialyl-LeX) conjugated to the cell-killing drug doxorubicin in combination with the chemotherapeutic agent TAXOTERE®. TAXOTERE® is the only FDA approved chemotherapy for the second line treatment of lung cancer. Initial data indicate an improved overall survival compared to TAXOTERE® alone. Out of the 62 patients who were recruited for the study, two-thirds received SGN-15 in combination with TAXOTERE® while the remaining one-third received TAXOTERE® alone. For the patients receiving SGN-15 in combination with TAXOTERE®, median overall survival was 7.3 months in comparison to 5.9 months for patients receiving TAXOTERE® alone. Overall survival at 1 year and 18 months was 29 and 18 percent respectively for patients receiving SNG-15 plus TAXOTERE® compared to 24 and 8 percent respectively for patients receiving TAXOTERE® alone. Further clinical trials are planned.

Preclinically, there has been some limited success in the use of monoclonal antibodies for melanoma. Very few of these antibodies have reached clinical trials and to date none have been approved or demonstrated favorable results in Phase III clinical trials.

The discovery of new drugs to treat disease is hindered by the lack of identification of relevant targets among the products of 30,000 known genes that could contribute to disease pathogenesis. In oncology research, potential drug targets are often selected simply due to the fact that they are over-expressed in tumor cells. Targets thus identified are then screened for interaction with a multitude of compounds. In the case of potential antibody therapies, these candidate compounds are usually derived from traditional methods of monoclonal antibody generation according to the fundamental principles laid down by Kohler and Milstein (1975, Nature, 256, 495-497, Kohler and Milstein). Spleen cells are collected from mice immunized with antigen (e.g. whole cells, cell fractions, purified antigen) and fused with immortalized hybridoma partners. The resulting hybridomas are screened and selected for secretion of antibodies which bind most avidly to the target. Many therapeutic and diagnostic antibodies directed against cancer cells, including Herceptin® and RITUXIMAB, have been produced using these methods and selected on the basis of their affinity. The flaws in this strategy are two-fold. Firstly, the choice of appropriate targets for therapeutic or diagnostic antibody binding is limited by the paucity of knowledge surrounding tissue specific carcinogenic processes and the resulting simplistic methods, such as selection by overexpression, by which these targets are identified. Secondly, the assumption that the drug molecule that binds to the receptor with the greatest affinity usually has the highest probability for initiating or inhibiting a signal may not always be the case.

Despite some progress with the treatment of breast and colon cancer, the identification and development of efficacious antibody therapies, either as single agents or co-treatments, have been inadequate for all types of cancer.

Prior Patents:

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to Anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single-chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an antinuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

SUMMARY OF THE INVENTION

This application utilizes methodology for producing patient specific anti-cancer antibodies taught in the U.S. Pat. No. 6,180,357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases. These antibodies can also be used for the prevention of cancer by way of prophylactic treatment. Unlike antibodies generated according to traditional drug discovery paradigms, antibodies generated in this way may target molecules and pathways not previously shown to be integral to the growth and/or survival of malignant tissue. Furthermore, the binding affinities of these antibodies are suited to requirements for initiation of the cytotoxic events that may not be amenable to stronger affinity interactions. Also, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, cytokines, interferons, target or reporter moieties or hematogenous cells, thereby forming an antibody conjugate. The CDMAB can be used alone or in combination with one or more CDMAB/chemotherapeutic agents.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and an anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity (ADCC) or complement dependent cytotoxicity (CDC). For example murine IgM and IgG2a antibodies can activate human complement by binding the C-1 component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

The cytotoxicity mediated through the Fc region requires the presence of effector cells, their corresponding receptors, or proteins e.g. NK cells, T cells and complement. In the absence of these effector mechanisms, the Fc portion of an antibody is inert. The Fc portion of an antibody may confer properties that affect the pharmacokinetics of an antibody in vivo, but in vitro this is not operative.

The cytotoxicity assays under which we test the antibodies do not have any of the effector mechanisms present, and are carried out in vitro. These assays do not have effector cells (NK, Macrophages, or T-cells) or complement present. Since these assays are completely defined by what is added together, each component can be characterized. The assays used herein contain only target cells, media and sera. The target cells do not have effector functions since they are cancer cells or fibroblasts. Without exogenous cells which have effector function properties there is no cellular elements that have this function. The media does not contain complement or any cells. The sera used to support the growth of the target cells do not have complement activity as disclosed by the vendors. Furthermore, in our own labs we have verified the absence of complement activity in the sera used. Therefore, our work evidences the fact that the effects of the antibodies are due entirely to the effects of the antigen binding which is mediated through the Fab. Effectively, the target cells are seeing and interacting with only the Fab, since they do not have receptors for the Fc. Although the hybridoma is secreting complete immunoglobulin which was tested with the target cells, the only part of the immunoglobulin that interacts with the cells are the Fab, which act as antigen binding fragments.

With respect to the instantly claimed antibodies and antigen binding fragments, the application, as filed, has demonstrated cellular cytotoxicity as evidenced by the data in FIG. 1. As pointed out above, and as herein confirmed via objective evidence, this effect was entirely due to binding by the Fab to the tumor cells.

Ample evidence exists in the art of antibodies mediating cytotoxicity due to direct binding of the antibody to the target antigen independent of effector mechanisms recruited by the Fc. The best evidence for this is in vitro experiments which do not have supplemental cells, or complement (to formally exclude those mechanisms). These types of experiments have been carried out with complete immunoglobulin, or with antigen binding fragments such as F(ab)'2 fragments. In these types of experiments, antibodies or antigen binding fragments can directly induce apoptosis of target cells such as in the case of anti-Her2 and anti-EGFR antibodies, both of which have been approved by the US FDA for marketing in cancer therapy.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are three additional mechanisms of antibody-mediated cancer cell killing. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost. The third is the effect of such antibodies on direct ligation of cell surface moieties that may lead to direct cell death, such as ligation of death receptors such as TRAIL R1 or TRAIL R2, or integrin molecules such as alpha V beta 3 and the like.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end 2003, there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

The present invention describes the development and use of AR58A314.1 identified by, its effect, in a cytotoxic assay and in a non-established animal model. This invention describes reagents that bind specifically to an epitope or epitopes present on the target molecule, and that also have in vitro cytotoxic properties, as a naked antibody, against malignant tumor cells but not normal cells, and which also directly mediate, as a naked antibody, inhibition of tumor growth. A further advance is that inclusion of this antibody in a library of anti-cancer antibodies will enhance the possibility of targeting tumors expressing different antigen markers by determination of the appropriate combination of different anti-cancer antibodies, to find the most effective in targeting and inhibiting growth and development of the tumors. It also represents an advance in cancer therapy since it has the potential to display similar anti-cancer properties in human patients. A further advance is that inclusion of these antibodies in a library of anti-cancer antibodies will enhance the possibility of targeting tumors expressing different antigen markers by determination of the appropriate combination of different anti-cancer antibodies, to find the most effective in targeting and inhibiting growth and development of the tumors.

In all, this invention teaches the use of the AR58A314.1 antigen as a target for a therapeutic agent, that when administered can reduce the tumor burden of a cancer expressing the antigen in a mammal. This invention also teaches the use of CDMAB (AR58A314.1), and their derivatives, and antigen binding fragments thereof, and cellular cytotoxicity inducing ligands thereof, to target their antigen to reduce the tumor burden of a cancer expressing the antigen in a mammal. Furthermore, this invention also teaches the use of detecting the AR58A314.1 antigen in cancerous cells that can be useful for the diagnosis, prediction of therapy, and prognosis of mammals bearing tumors that express this antigen.

Accordingly, it is an objective of the invention to utilize a method for producing cancerous disease modifying antibodies (CDMAB) raised against cancerous cells derived from a particular individual, or one or more particular cancer cell lines, which CDMAB are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies, ligands and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies which are useful for in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 compares the percentage cytotoxicity and binding levels of the hybridoma supernatants against cell lines MDA-MB-231 (MB-231), OVCAR-3, SW1116, Lovo, and CCD-27sk.

FIG. 2 represents binding of AR58A314.1 and the anti-EGFR control to cancer and normal cell lines. The data is tabulated to present the mean fluorescence intensity as a fold increase above isotype control.

FIG. 8 is a comparison of AR58A314.1 versus positive and negative controls on a human tumor and normal tissue micro array.

FIG. 9. Representative micrographs showing the binding pattern on lung tumor tissue obtained with AR58A314.1 (A) or the isotype control antibody (B) and on lung normal tissue obtained with AR58A314.1 (C) or anti-actin (D) from a human tissue microarray. AR58A314.1 displayed positive staining for the tumor cells and negative staining on the normal tissue. Magnification is 200×.

FIG. 10 is a comparison of AR58A314.1 versus positive and negative controls on a human normal tissue micro array.

DETAILED DESCRIPTION OF THE INVENTION

Figure 3:
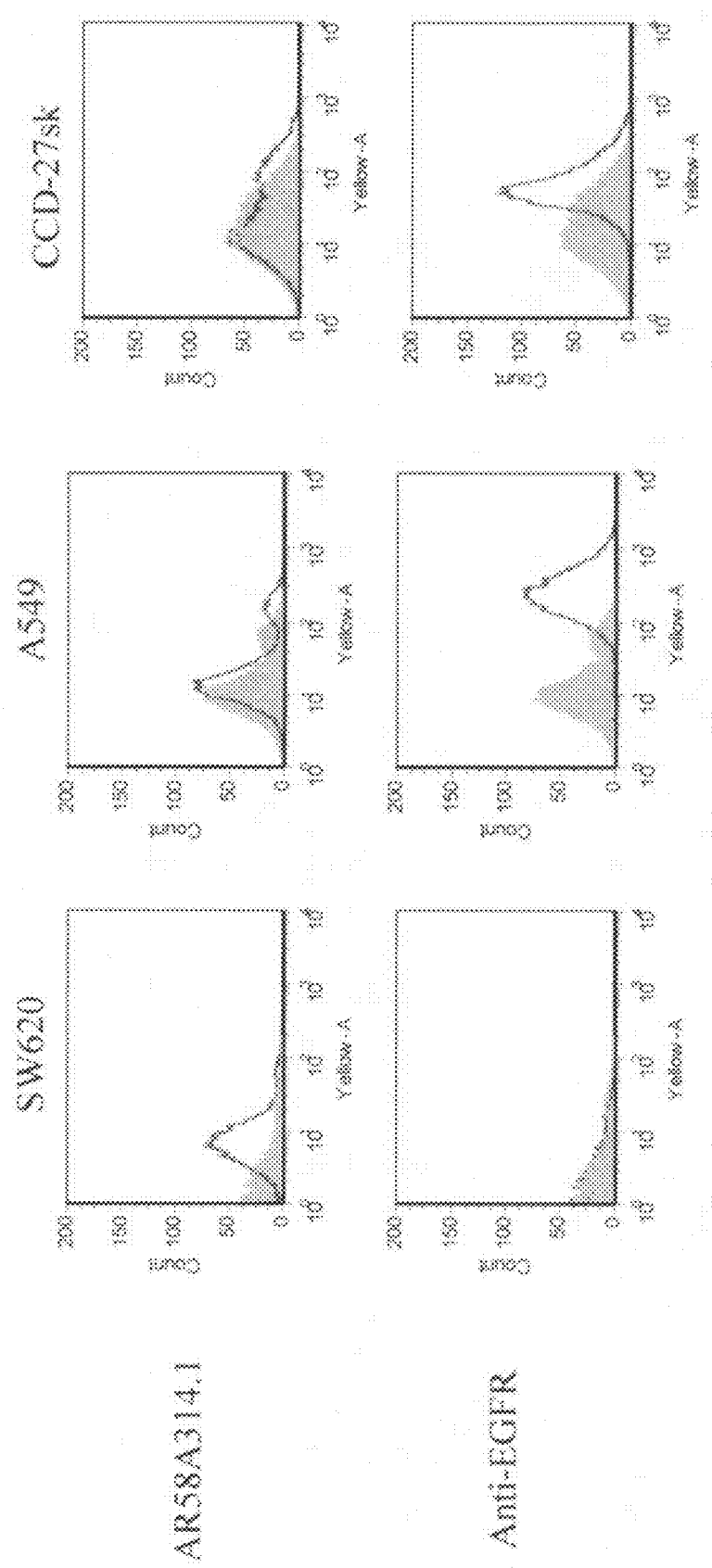
FIG. 3 includes representative FACS histograms of AR58A314.1 and anti-EGFR antibodies directed against several cancer and non-cancer cell lines.

In general, the following words or phrases have the indicated definition when used in the summary, description, examples, and claims.

The term "antibody" is used in the broadest sense and specifically covers, for example, single monoclonal antibodies (including agonist, antagonist, and neutralizing antibodies, de-immunized, murine, chimeric or humanized antibodies), antibody compositions with polyepitopic specificity, single-chain antibodies, diabodies, triabodies, immunoconjugates and antibody fragments (see below).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., Nature, 256:495 (1975), or may be made by recombinant DNA methods (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

"Antibody fragments" comprise a portion of an intact antibody, preferably comprising the antigen-binding or variable region thereof. Examples of antibody fragments include less than full length antibodies, Fab, Fab', F(ab')$_2$, and Fv fragments; diabodies; linear antibodies; single-chain antibody molecules; single-chain antibodies, single domain antibody molecules, fusion proteins, recombinant proteins and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called a, d, e, ?, and μ, respectively. The subunit structures and three-dimensional configurations of different classes of immunoglobulins are well known.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express Fc?RIII only, whereas monocytes express Fc?RI, Fc?RII and Fc?RIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998).

"Effector cells" are leukocytes which express one or more FcRs and perform effector functions. Preferably, the cells express at least Fc?RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the Fc?RI, Fc?RII, and Fc?RIII subclasses, including allelic variants and alternatively spliced forms of these receptors. Fc?RII receptors include Fc?RIIA (an "activating receptor") and Fc?RIIB (an "inhibiting receptor"), which have similar amino acid sequences that differ primarily in the cytoplasmic domains thereof. Activating receptor Fc?RIIA contains an immunoreceptor tyrosine-based activation motif (ITAM) in its cytoplasmic domain. Inhibiting receptor Fc?RIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, Annu. Rev. Immunol 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *Eur. J. Immunol.* 24:2429 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of proteins of immunological Interest,* 5th Ed. Public Health Service, National Institutes of Health, Bethesda, Md. (1991)) and/or those residues from a "hypervariable loop" (e.g. residues 2632 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CHI) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (?) and lambda (?), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "triabodies" or "trivalent trimers" refers to the combination of three single chain antibodies. Triabodies are constructed with the amino acid terminus of a $V_L$ or $V_H$ domain, i.e., without any linker sequence. A triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful as a therapeutic or diagnostic agent in targeting a cell expressing the antigen. Where the antibody is one which binds the antigen of interest, it will usually preferentially bind the antigen of interest as opposed to other proteins, and does not include incidental binding such as non-specific Fc contact, or binding to post-translational modifications common to other antigens and may be one which does not significantly cross-react with other proteins. Methods, for the detection of an antibody that binds an antigen of interest, are well known in the art and can include but are not limited to assays such as FACS, cell ELISA and Western blot.

As used herein, the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Treatment or treating" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Hence, the mammal to be treated herein may have been diagnosed as having the disorder or may be predisposed or susceptible to the disorder.

The terms "cancer" and "cancerous" refer to or describe the physiological condition in mammals that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, camomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carnofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2?-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

"Mammal" for purposes of treatment refers to any animal classified as a mammal, including humans, mice, SCID or nude mice or strains of mice, domestic and farm animals, and zoo, sports, or pet animals, such as sheep, dogs, horses, cats, cows, etc. Preferably, the mammal herein is human.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., Nucl. Acids Res., 14:5399-5407, 1986. They are then purified on polyacrylamide gels.

In accordance with the present invention, "humanized" and/or "chimeric" forms of non-human (e.g. murine) immunoglobulins refer to antibodies which contain specific chimeric immunoglobulins, immunoglobulin chains or fragments thereof (such as Fv, Fab, Fab', F(ab')$_2$ or other antigen-binding subsequences of antibodies) which results in the decrease of a human anti-mouse antibody (HAMA), human anti-chimeric antibody (HACA) or a human anti-human antibody (HAHA) response, compared to the original antibody, and contain the requisite portions (e.g. CDR(s), antigen binding region(s), variable domain(s) and so on) derived from said non-human immunoglobulin, necessary to reproduce the desired effect, while simultaneously retaining binding characteristics which are comparable to said non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

"De-immunized" antibodies are immunoglobulins that are non-immunogenic, or less immunogenic, to a given species. De-immunization can be achieved through structural alterations to the antibody. Any de-immunization technique known to those skilled in the art can be employed. One suitable technique for de-immunizing antibodies is described, for example, in WO 00/34317 published Jun. 15, 2000.

An antibody which induces "apoptosis" is one which induces programmed cell death by any means, illustrated by but not limited to binding of annexin V, caspase activity, fragmentation of DNA, cell shrinkage, dilation of endoplasmic reticulum, cell fragmentation, and/or formation of membrane vesicles (called apoptotic bodies).

As used herein "antibody induced cytotoxicity" is understood to mean the cytotoxic effect derived from the hybridoma supernatant or antibody produced by the hybridoma deposited with the IDAC as accession number 141205-02 which effect is not necessarily related to the degree of binding.

Throughout the instant specification, hybridoma cell lines, as well as the isolated monoclonal antibodies which are produced therefrom, are alternatively referred to by their internal designation, AR58A314.1 or Depository Designation, IDAC 141205-02.

As used herein "antibody-ligand" includes a moiety which exhibits binding specificity for at least one epitope of the target antigen, and which may be an intact antibody molecule, antibody fragments, and any molecule having at least an antigen-binding region or portion thereof (i.e., the variable portion of an antibody molecule), e.g., an Fv molecule, Fab molecule, Fab' molecule, F(ab').sub.2 molecule, a bispecific antibody, a fusion protein, or any genetically engineered molecule which specifically recognizes and binds at least one epitope of the antigen bound by the isolated monoclonal antibody produced by the hybridoma cell line designated as IDAC 141205-02 (the IDAC 141205-02 antigen).

As used herein "cancerous disease modifying antibodies" (CDMAB) refers to monoclonal antibodies which modify the cancerous disease process in a manner which is beneficial to the patient, for example by reducing tumor burden or prolonging survival of tumor bearing individuals, and antibody-ligands thereof.

A "CDMAB related binding agent", in its broadest sense, is understood to include, but is not limited to, any form of human or non-human antibodies, antibody fragments, antibody ligands, or the like, which competitively bind to at least one CDMAB target epitope.

A "competitive binder" is understood to include any form of human or non-human antibodies, antibody fragments, antibody ligands, or the like which has binding affinity for at least one CDMAB target epitope.

Tumors to be treated include primary tumors and metastatic tumors, as well as refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents but recur up to five years, sometimes up to ten years or longer after treatment is discontinued.

Tumors that can be treated include tumors that are not vascularized, or not yet substantially vascularized, as well as vascularized tumors. Examples of solid tumors, which can be accordingly treated, include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma.

As used herein "antigen-binding region" means a portion of the molecule which recognizes the target antigen.

As used herein "competitively inhibits" means being able to recognize and bind a determinant site to which the monoclonal antibody produced by the hybridoma cell line designated as IDAC 141205-02, (the IDAC 141205-02 antibody) is directed using conventional reciprocal antibody competition assays. (Belanger L., Sylvestre C. and Dufour D. (1973), Enzyme linked immunoassay for alpha fetoprotein by competitive and sandwich procedures. Clinica Chimica Acta 48, 15).

As used herein "target antigen" is the IDAC 141205-02 antigen or portions thereof.

As used herein, an "immunoconjugate" means any molecule or CDMAB such as an antibody chemically or biologically linked to cytotoxins, radioactive agents, cytokines, interferons, target or reporter moieties, enzymes, toxins, anti-tumor drugs or therapeutic agents. The antibody or CDMAB may be linked to the cytotoxin, radioactive agent, cytokine, interferon, target or reporter moiety, enzyme, toxin, anti-tumor drug or therapeutic agent at any location along the molecule so long as it is able to bind its target. Examples of immunoconjugates include antibody toxin chemical conjugates and antibody-toxin fusion proteins.

Radioactive agents suitable for use as anti-tumor agents are known to those skilled in the art. For example, 131I or 211At is used. These isotopes are attached to the antibody using conventional techniques (e.g. Pedley et al., Br. J. Cancer 68, 69-73 (1993)). Alternatively, the anti-tumor agent which is attached to the antibody is an enzyme which activates a prodrug. A prodrug may be administered which will remain in its inactive form until it reaches the tumor site where it is converted to its cytotoxin form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4) or tumor necrosis factor alpha (TNF-a). The antibody targets the cytokine to the tumor so that the cytokine mediates damage to or destruction of the tumor without affecting other tissues. The cytokine is fused to the antibody at the DNA level using conventional recombinant DNA techniques. Interferons may also be used.

As used herein, a "fusion protein" means any chimeric protein wherein an antigen binding region is connected to a biologically active molecule, e.g., toxin, enzyme, fluorescent proteins, luminescent marker, polypeptide tag, cytokine, interferon, target or reporter moiety or protein drug.

The invention further contemplates CDMAB of the present invention to which target or reporter moieties are linked. Target moieties are first members of binding pairs. Anti-tumor agents, for example, are conjugated to second members of such pairs and are thereby directed to the site where the antigen-binding protein is bound. A common example of such a binding pair is avidin and biotin. In a preferred embodiment, biotin is conjugated to the target antigen of the CDMAB of the present invention, and thereby provides a target for an anti-tumor agent or other moiety which is conjugated to avidin or streptavidin. Alternatively, biotin or another such moiety is linked to the target antigen of the CDMAB of the present invention and used as a reporter, for example in a diagnostic system where a detectable signal-producing agent is conjugated to avidin or streptavidin.

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible region, and can be substrates or degradation products of enzyme catalyzed reactions.

Moreover, included within the scope of the present invention is use of the present CDMAB in vivo and in vitro for investigative or diagnostic methods, which are well known in the art. In order to carry out the diagnostic methods as contemplated herein, the instant invention may further include kits, which contain CDMAB of the present invention. Such kits will be useful for identification of individuals at risk for certain type of cancers by detecting over-expression of the CDMAB's target antigen on cells of such individuals.

Diagnostic Assay Kits

It is contemplated to utilize the CDMAB of the present invention in the form of a diagnostic assay kit for determining the presence of a tumor. The tumor will generally be detected in a patient based on the presence of one or more tumor-specific antigens, e.g. proteins and/or polynucleotides which encode such proteins in a biological sample, such as blood, sera, urine and/or tumor biopsies, which samples will have been obtained from the patient.

The proteins function as markers which indicate the presence or absence of a particular tumor, for example a colon, breast, lung or prostate tumor. It is further contemplated that the antigen will have utility for the detection of other cancerous tumors. Inclusion in the diagnostic assay kits of binding agents comprised of CDMABs of the present invention, or CDMAB related binding agents, enables detection of the level of antigen that binds to the agent in the biological sample. Polynucleotide primers and probes may be used to detect the level of mRNA encoding a tumor protein, which is also indicative of the presence or absence of a cancer. In order for the binding assay to be diagnostic, data will have been generated which correlates statistically significant levels of antigen, in relation to that present in normal tissue, so as to render the recognition of binding definitively diagnostic for the presence of a cancerous tumor. It is contemplated that a plurality of formats will be useful for the diagnostic assay of the present invention, as are known to those of ordinary skill in the art, for using a binding agent to detect polypeptide markers in a sample. For example, as illustrated in Harlow and Lane, Antibodies: A Laboratory Manual, Cold Spring Harbor Laboratory, 1988. Further contemplated are any and all combinations, permutations or modifications of the aforedescribed diagnostic assay formats.

The presence or absence of a cancer in a patient will typically be determined by (a) contacting a biological sample obtained from a patient with a binding agent; (b) detecting in the sample a level of polypeptide that binds to the binding agent; and (c) comparing the level of polypeptide with a predetermined cut-off value.

In an illustrative embodiment, it is contemplated that the assay will involve the use of a CDMAB based binding agent immobilized on a solid support to bind to and remove the polypeptide from the remainder of the sample. The bound polypeptide may then be detected using a detection reagent that contains a reporter group and specifically binds to the binding agent/polypeptide complex. Illustrative detection reagents may include a CDMAB based binding agent that specifically binds to the polypeptide or an antibody or other agent that specifically binds to the binding agent, such as an anti-immunoglobulin, protein G, protein A or a lectin. In an alternative embodiment, it is contemplated that a competitive assay may be utilized, in which a polypeptide is labeled with a reporter group and allowed to bind to the immobilized binding agent after incubation of the binding agent with the sample. Indicative of the reactivity of the sample with the immobilized binding agent, is the extent to which components of the sample inhibit the binding of the labeled polypeptide to the binding agent. Suitable polypeptides for use within such assays include full length tumor-specific proteins and/or portions thereof, to which the binding agent has binding affinity.

The diagnostic kit will be provided with a solid support which may be in the form of any material known to those of ordinary skill in the art to which the protein may be attached. Suitable examples may include a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

It is contemplated that the binding agent will be immobilized on the solid support using a variety of techniques known to those of skill in the art, which are amply described in the patent and scientific literature. The term "immobilization" refers to both noncovalent association, such as adsorption, and covalent attachment, which, in the context of the present invention, may be a direct linkage between the agent and functional groups on the support, or may be a linkage by way of a cross-linking agent. In a preferred, albeit non-limiting embodiment, immobilization by adsorption to a well in a microtiter plate or to a membrane is preferable. Adsorption may be achieved by contacting the binding agent, in a suitable buffer, with the solid support for a suitable amount of time. The contact time may vary with temperature, and will generally be within a range of between about 1 hour and about 1 day.

Covalent attachment of binding agent to a solid support would ordinarily be accomplished by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12 A13).

It is further contemplated that the diagnostic assay kit will take the form of a two-antibody sandwich assay. This assay may be performed by first contacting an antibody, e.g. the instantly disclosed CDMAB that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

In a specific embodiment, it is contemplated that once the antibody is immobilized on the support as described above, the remaining protein binding sites on the support will be blocked, via the use of any suitable blocking agent known to those of ordinary skill in the art, such as bovine serum albumin or Tween 20™ (Sigma Chemical Co., St. Louis, Mo.). The immobilized antibody would then be incubated with the sample, and polypeptide would be allowed to bind to the antibody. The sample could be diluted with a suitable diluent, such as phosphate-buffered saline (PBS) prior to incubation. In general, an appropriate contact time (i.e., incubation time) would be selected to correspond to a period of time sufficient to detect the presence of polypeptide within a sample obtained from an individual with the specifically selected tumor. Preferably, the contact time is sufficient to achieve a level of binding that is at least about 95 percent of that achieved at equilibrium between bound and unbound polypeptide. Those of ordinary skill in the art will recognize that the time necessary to achieve equilibrium may be readily determined by assaying the level of binding that occurs over a period of time.

It is further contemplated that unbound sample would then be removed by washing the solid support with an appropriate buffer. The second antibody, which contains a reporter group, would then be added to the solid support. Incubation of the detection reagent with the immobilized antibody-polypeptide complex would then be carried out for an amount of time sufficient to detect the bound polypeptide. Subsequently, unbound detection reagent would then be removed and bound detection reagent would be detected using the reporter group. The method employed for detecting the reporter group is necessarily specific to the type of reporter group selected, for example for radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

In order to utilize the diagnostic assay kit of the present invention to determine the presence or absence of a cancer, such as prostate cancer, the signal detected from the reporter group that remains bound to the solid support would generally be compared to a signal that corresponds to a predetermined cut-off value. For example, an illustrative cut-off value for the detection of a cancer may be the average mean signal obtained when the immobilized antibody is incubated with samples from patients without the cancer. In general, a sample generating a signal that is about three standard deviations above the predetermined cut-off value would be considered positive for the cancer. In an alternate embodiment, the cut-off value might be determined by using a Receiver Operator Curve, according to the method of Sackett et al., Clinical Epidemiology. A Basic Science for Clinical Medicine, Little Brown and Co., 1985, p. 106-7. In such an embodiment, the cut-off value could be determined from a plot of pairs of true positive rates (i.e., sensitivity) and false positive rates (100 percent-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

It is contemplated that the diagnostic assay enabled by the kit will be performed in either a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound will be immersed in a solution containing the sample. The sample migrates along the membrane through a region containing second binding agent and to the area of immobilized binding agent. Concentration of the second binding agent at the area of immobilized antibody indicates the presence of a cancer. Generation of a pattern, such as a line, at the binding site, which can be read visually, will be indicative of a positive test. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in the instant diagnostic assay are the instantly disclosed antibodies, antigen-binding fragments thereof, and any CDMAB related binding agents as herein described. The amount of antibody immobilized on the membrane will be any amount effective to produce a diagnostic assay, and may range from about 25 nanograms to about 1 microgram. Typically such tests may be performed with a very small amount of biological sample.

Additionally, the CDMAB of the present invention may be used in the laboratory for research due to its ability to identify its target antigen.

In order that the invention herein described may be more fully understood, the following description is set forth.

The present invention provides CDMAB (i.e., IDAC 141205-02 CDMAB) which specifically recognize and bind the IDAC 141205-02 antigen.

The CDMAB of the isolated monoclonal antibody produced by the hybridoma deposited with the IDAC as accession number 141205-02 may be in any form as long as it has an antigen-binding region which competitively inhibits the immunospecific binding of the isolated monoclonal antibody produced by hybridoma IDAC 141205-02 to its target antigen. Thus, any recombinant proteins (e.g., fusion proteins wherein the antibody is combined with a second protein such as a lymphokine or a tumor inhibitory growth factor) having the same binding specificity as the IDAC 141205-02 antibody fall within the scope of this invention.

In one embodiment of the invention, the CDMAB is the IDAC 141205-02 antibody.

In other embodiments, the CDMAB is an antigen binding fragment which may be a Fv molecule (such as a single-chain Fv molecule), a Fab molecule, a Fab' molecule, a F(ab')2 molecule, a fusion protein, a bispecific antibody, a heteroantibody or any recombinant molecule having the antigen-binding region of the IDAC 141205-02 antibody. The CDMAB of the invention is directed to the epitope to which the IDAC 141205-02 monoclonal antibody is directed.

The CDMAB of the invention may be modified, i.e., by amino acid modifications within the molecule, so as to produce derivative molecules. Chemical modification may also be possible. Modification by direct mutation, methods of affinity maturation, phage display or chain shuffling may also be possible.

Affinity and specificity-can be modified or improved by mutating CDR and/or phenylalanine tryptophan (FW) residues and screening for antigen binding sites having the desired characteristics (e.g., Yang et al., J. Mol. Biol., (1995) 254: 392-403). One way is to randomize individual residues or combinations of residues so that in a population of otherwise identical antigen binding sites, subsets of from two to twenty amino acids are found at particular positions. Alternatively, mutations can be induced over a range of residues by error prone PCR methods (e.g., Hawkins et al., J. Mol. Biol., (1992) 226: 889-96). In another example, phage display vectors containing heavy and light chain variable region genes can be propagated in mutator strains of *E. coli* (e.g., Low et al., J. Mol. Biol., (1996) 250: 359-68). These methods of mutagenesis are illustrative of the many methods known to one of skill in the art.

Another manner for increasing affinity of the antibodies of the present invention is to carry out chain shuffling, where the heavy or light chain are randomly paired with other heavy or light chains to prepare an antibody with higher affinity. The various CDRs of the antibodies may also be shuffled with the corresponding CDRs in other antibodies.

Derivative molecules would retain the functional property of the polypeptide, namely, the molecule having such substitutions will still permit the binding of the polypeptide to the IDAC 141205-02 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

EXAMPLE 1

Hybridoma Production—Hybridoma Cell Line AR58A314.1

The hybridoma cell line AR58A314.1 was deposited, in accordance with the Budapest Treaty, with the International Depository Authority of Canada (IDAC), Bureau of Microbiology, Health Canada, 1015 Arlington Street, Winnipeg, Manitoba, Canada, R3E 3R2, on Dec. 14, 2005, under Accession Number 141205-02. In accordance with 37 CFR 1.808, the depositors assure that all restrictions imposed on the availability to the public of the deposited materials will be irrevocably removed upon the granting of a patent.

To produce the hybridoma that produces the anti-cancer antibody AR58A314.1, a single cell suspension of frozen colon tumor tissue (Genomics Collaborative, Cambridge, Mass.) was prepared in PBS. IMMUNEASY™ (Qiagen, Venlo, Netherlands) adjuvant was prepared for use by gentle mixing. Five to seven week old BALB/c mice were immunized by injecting subcutaneously, 2 million cells in 50 microliters of the antigen-adjuvant. Recently prepared antigen-adjuvant was used to boost the immunized mice intraperitoneally, 2 and 5 weeks after the initial immunization, with 2 million cells in 50 microliters. A spleen was used for fusion three days after the last immunization. The hybridomas were prepared by fusing the isolated splenocytes with NSO-1 myeloma partners. The supernatants from the fusions were tested from subclones of the hybridomas.

To determine whether the antibodies secreted by the hybridoma cells are of the IgG or IgM isotype, an ELISA assay was employed. 100 microliters/well of goat anti-mouse IgG+IgM (H+L) at a concentration of 2.4 micrograms/mL in coating buffer (0.1 M carbonate/bicarbonate buffer, pH 9.2-9.6) at 4° C. was added to the ELISA plates overnight. The plates were washed thrice in washing buffer (PBS+0.05 percent Tween-20). 100 microliters/well blocking buffer (5 percent milk in wash buffer) was added to the plate for 1 hour at room temperature and then washed thrice in washing buffer. 100 microliters/well of hybridoma supernatant was added and the plate incubated for 1 hour at room temperature. The plates were washed thrice with washing buffer and 1/100,000 dilution of either goat anti-mouse IgG or IgM horseradish peroxidase conjugate (diluted in PBS containing 1 percent milk), 100 microliters/well, was added. After incubating the plate for 1 hour at room temperature the plate was washed thrice with washing buffer. 100 microliters/well of TMB solution was incubated for 1-3 minutes at room temperature. The color reaction was terminated by adding 50 microliters/well 2M $H_2SO_4$ and the plate was read at 450 nm with a Perkin-Elmer HTS7000 plate reader. As indicated in FIG. 1, the AR58A314.1 hybridoma secreted primarily antibodies of the IgG isotype.

To determine the subclass of antibody secreted by the hybridoma cells, an isotyping experiment was performed using a Mouse Monoclonal Antibody Isotyping Kit (GE Healthcare, Baie d'Urfé, Quebec). Antibody-containing hybridoma supernatant was added to a test tube (in a 1:10 dilution with TBS-T) with an isotyping strip carrying goat antibody specific for the different types of peptide chain. The tube was agitated for 15 minutes. The strip was then washed twice with TBS-T for 5 minutes with agitation. A peroxidase-labelled, species-specific anti-mouse antibody was added (in a 1:500 dilution with TBS-T) to the test tube for 15 minutes, to detect the monoclonal antibody bound to the goat antibody on the stick. The strip was again washed twice with TBS-T for 5 minutes with agitation. The peroxidase-labelled antibody bound to the strip was then detected using a peroxidase substrate system. One 30 mg tablet of 4-chloro-1-napthol was dissolved in 10 mL cold ethanol, and one drop of hydrogen peroxide solution (30 percent v/v) was diluted in 50 mL TBS. The two solutions were combined immediately before use, and 3 mL was added to the isotyping strip for 15 minutes with agitation. The substrate solution was then discarded and the strip was washed three times with 5 mL distilled water with agitation. The typing stick was then removed from the test tube and analysed for results. The anti-cancer antibody AR58A314.1 is of the IgG1, kappa isotype.

After one round of limiting dilution, hybridoma supernatants were tested for antibodies that bound to target cells in a cell ELISA assay. One human breast cancer cell line, 1 human ovarian cancer cell line, 2 human colon cancer cell lines, and 1 human normal skin cell line were tested: MDA-MB-231 (MB-231), OVCAR-3, SW1116, Lovo, and CCD-27sk, respectively. The cell lines were obtained from the American Type Tissue Collection (ATCC, Manassas, Va.). The plated cells were fixed prior to use. The plates were washed thrice with PBS containing $MgCl_2$ and $CaCl_2$ at room temperature. 100 microliters of 2 percent paraformaldehyde diluted in PBS was added to each well for 10 minutes at room temperature and then discarded. The plates were again washed with PBS containing $MgCl_2$ and $CaCl_2$ three times at room temperature. Blocking was done with 100 microliters/well of 5 percent milk in wash buffer (PBS+0.05 percent Tween-20) for 1 hour at room temperature. The plates were washed thrice with wash buffer and the hybridoma supernatant was added at 75 microliters/well for 1 hour at room temperature. The plates were washed 3 times with wash buffer and 100 microliters/well of 1/25,000 dilution of goat anti-mouse IgG antibody conjugated to horseradish peroxidase (diluted in PBS containing 1 percent milk) was added. After 1 hour incubation at room temperature the plates were washed 3 times with wash buffer and 100 microliter/well of TMB substrate was incubated for 1-3 minutes at room temperature. The reaction was terminated with 50 microliters/well 2M $H_2SO_4$ and the plate read at 450 nm with a Perkin-Elmer HTS7000 plate reader. The results as tabulated in FIG. 2 were expressed as the number of folds above background compared to an in-house IgG isotype control that has previously been shown not to bind to the cell lines tested. The antibodies from the hybridoma AR58A314.1 showed no detectable binding to any of the cell lines tested.

In conjunction with testing for antibody binding, the cytotoxic effect of the hybridoma supernatants was tested in the cell lines: MDA-MB-231 (MB-231), OVCAR-3, SW1116, Lovo and CCD-27sk. Calcein AM was obtained from Molecular Probes (Eugene, Oreg.). The assays were performed according to the manufacturer's instructions with the changes outlined below. Cells were plated before the assay at the predetermined appropriate density. After 2 days, 75 microliters of supernatant from the hybridoma microtiter plates were transferred to the cell plates and incubated in a 5 percent $CO_2$ incubator for 5 days. The wells that served as the positive controls were aspirated until empty and 100 microliters of sodium azide ($NaN_3$) or cycloheximide or anti-EGFR (c225; 5 micrograms/mL) was added. After 5 days of treatment, the plates were then emptied by inverting and blotting dry. Room temperature DPBS (Dulbecco's phosphate buffered saline) containing $MgCl_2$ and $CaCl_2$ was dispensed into each well from a multichannel squeeze bottle, tapped 3 times, emptied by inversion and then blotted dry. 50 microliters of the fluorescent calcein dye diluted in DPBS containing $MgCl_2$ and $CaCl_2$ was added to each well and incubated at 37° C. in a 5 percent $CO_2$ incubator for 30 minutes. The plates were read in a Perkin-Elmer HTS7000 fluorescence plate reader and the data was analyzed in Microsoft Excel. The results are tabulated in FIG. 1. Supernatant from the AR58A314.1 hybridoma produced specific cytotoxicity of 13 percent on the OVCAR-3 cells, 13 percent on the SW1116 cells, and 12 percent on the Lovo cells. The cytotoxicity on the OVCAR-3 cells was 24 and 43 percent of the cytotoxicity obtained with the positive controls sodium azide and cyclohexamide, respectively. The cytotoxicity of 13 percent on the SW1116 cells was 41 and 65 percent of the cytotoxicity obtained with c225 and cyclohexamide, respectively. Finally, the cytotoxicity of 12 percent on the Lovo cells was 26 percent of the cytotoxicity obtained with cyclohexamide. Results from FIG. 1 demonstrated that the cytotoxic effects of AR58A314.1 are not proportional to the binding levels on the cancer cell types. As tabulated in FIG. 1, AR58A314.1 did not produce cytotoxicity in the CCD-27sk normal cell line. The known non-specific cytotoxic agents cycloheximide and $NaN_3$ and the anti-EGFR antibody c225 generally produced cytotoxicity as expected.

EXAMPLE 2

In Vitro Binding

AR58A314.1 monoclonal antibody was produced by culturing the hybridoma in CL-1000 flasks (BD Biosciences, Oakville, ON) with collections and reseeding occurring twice/week. Standard antibody purification procedures with Protein G Sepharose 4 Fast Flow (Amersham Biosciences, Baie d'Urfé, QC) were followed. It is within the scope of this invention to utilize monoclonal antibodies that are de-immunized, humanized, chimeric or murine.

Binding of AR58A314.1 to breast (MB-231), colon (DLD-1, Lovo, SW1116 and SW620), lung (A549), prostate (PC-3), ovarian (OVCAR-3) and pancreatic (AsPC-1 and BxPC-3) cancer, and non-cancer cell lines from skin (CCD-27sk) and lung (Hs888.Lu) was assessed by flow cytometry (FACS). All cell lines were obtained from the American Type Tissue Collection (ATCC, Manassas, Va.).

Cells were prepared for FACS by initially washing the cell monolayer with DPBS (without $Ca^{++}$ and $Mg^{++}$). Cell dissociation buffer (INVITROGEN, Burlington, ON) was then used to dislodge the cells from their cell culture plates at 37° C. After centrifugation and collection, the cells were resuspended in DPBS containing $MgCl_2$, $CaCl_2$ and 2 percent fetal bovine serum at 4° C. (staining media) and counted, aliquoted to appropriate cell density, spun down to pellet the cells and resuspended in staining media at 4° C. in the presence of test antibody (AR58A314.1) or control antibodies (isotype control, anti-EGFR). Isotype control and the test antibody were assessed at 20 micrograms/mL whereas anti-EGFR was assessed at 5 micrograms/mL on ice for 30 minutes. Prior to the addition of Alexa Fluor 546-conjugated secondary antibody the cells were washed once with staining media. The Alexa Fluor 546-conjugated antibody in staining media was then added for 30 minutes at 4° C. The cells were then washed for the final time and resuspended in fixing media (staining media containing 1.5 percent paraformaldehyde). Flow cytometric acquisition of the cells was assessed by running samples on a FACSarray™ using the FACSarray™ System Software (BD Biosciences, Oakville, ON). The forward (FSC) and side scatter (SSC) of the cells were set by adjusting the voltage and amplitude gains on the FSC and SSC detectors. The detectors for the fluorescence (Alexa-546) channel was adjusted by running unstained cells such that cells had a uniform peak with a median fluorescence intensity of approximately 1-5 units. For each sample, approximately 10,000 gated events (stained fixed cells) were acquired for analysis and the results are presented in FIG. 3.

FIG. 2 presents the mean fluorescence intensity fold increase above isotype control. Representative histograms of AR58A314.1 antibodies were compiled for FIG. 3. AR58A314.1 showed binding to the colon cancer cell lines DLD-1, Lovo, SW1116 and SW620 (1.8-fold, 2.0-fold, 2.1-fold and 8.5-fold) and the ovarian cancer cell line (OVCAR-3). Binding to the CCD-27sk normal skin and Hs888.Lu cell lines was not detectable under these conditions. From Example 1, it was evident that the binding of AR58A310.1 to the OVCAR-3 ovarian and SW1116 and Lovo colon cancer cancer cell lines is not detectable using cell ELISA. However, detectable binding was demonstrated using FACS illustrating that FACS is a more sensitive binding assay under these conditions.

EXAMPLE 3

In vivo Tumor Experiments with A549 Cells

Figure 4:
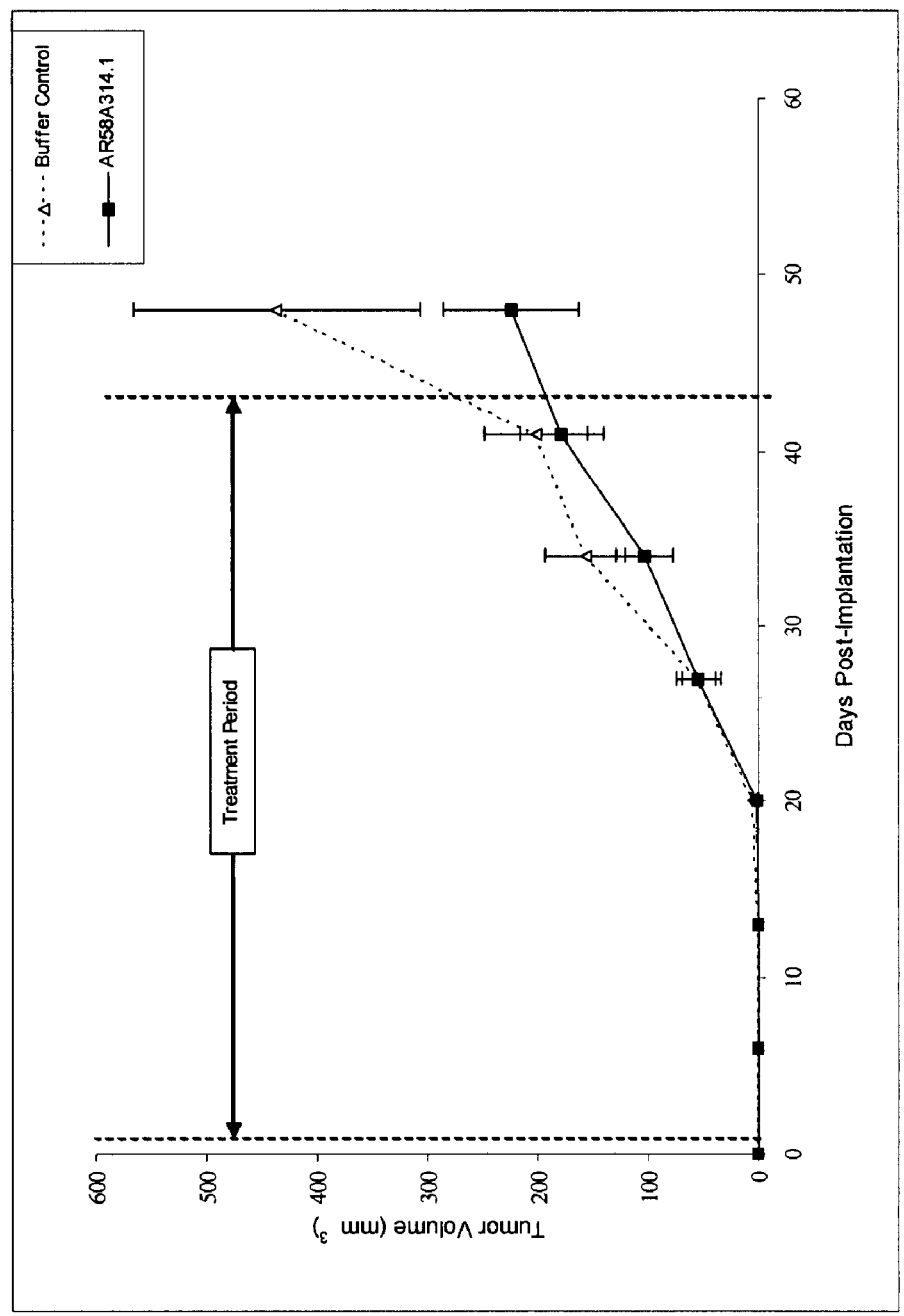
FIG. 4 demonstrates the effect of AR58A314.1 on tumor growth in a prophylactic A549 lung cancer model. The vertical dashed lines indicate the period during which the antibody was administered. Data points represent the mean +/− SEM.
Figure 5:
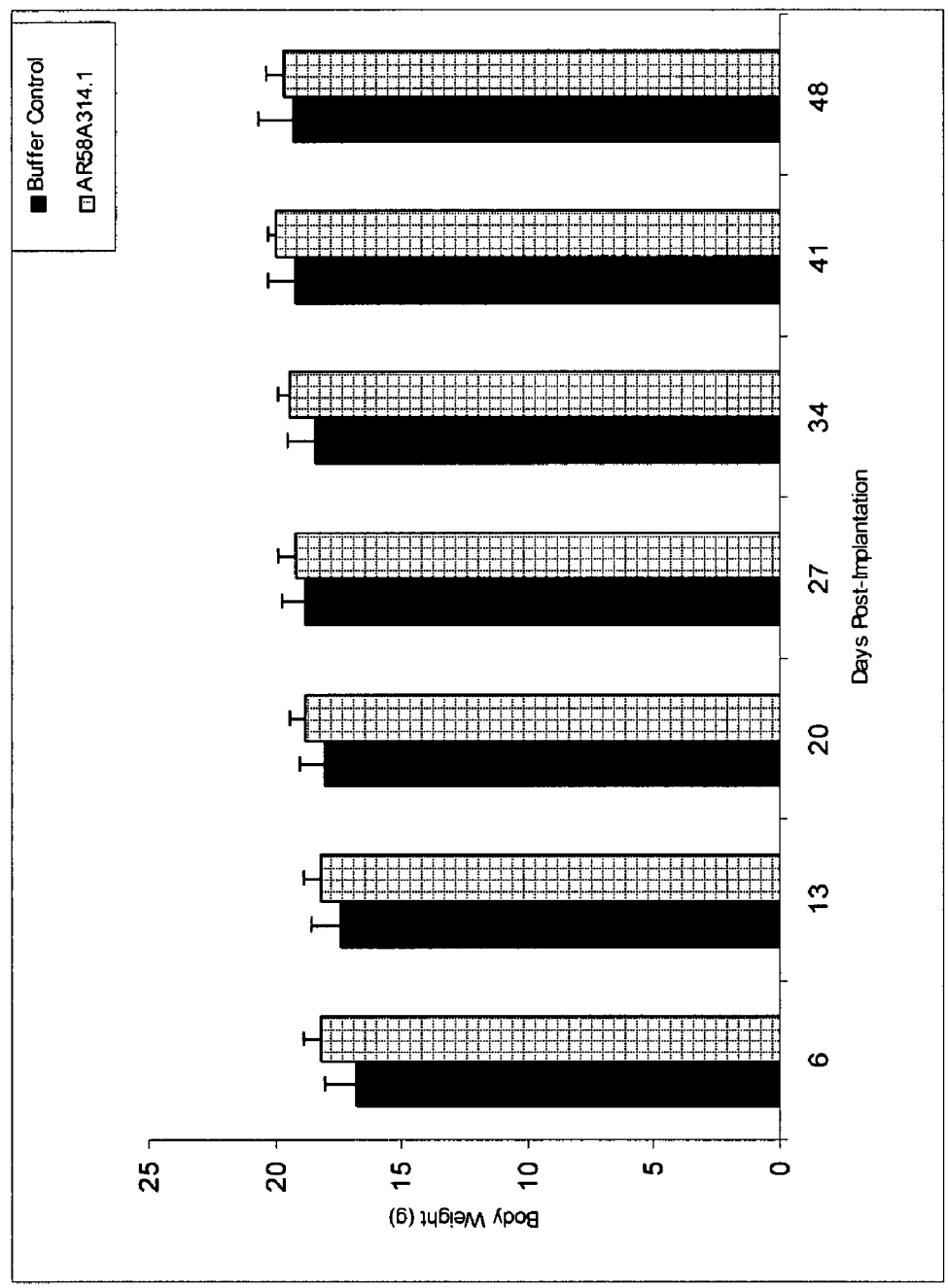
FIG. 5 demonstrates the effect of AR58A314.1 on body weight in a prophylactic A549 lung cancer model. Data points represent the mean +/− SEM.
Figure 6:
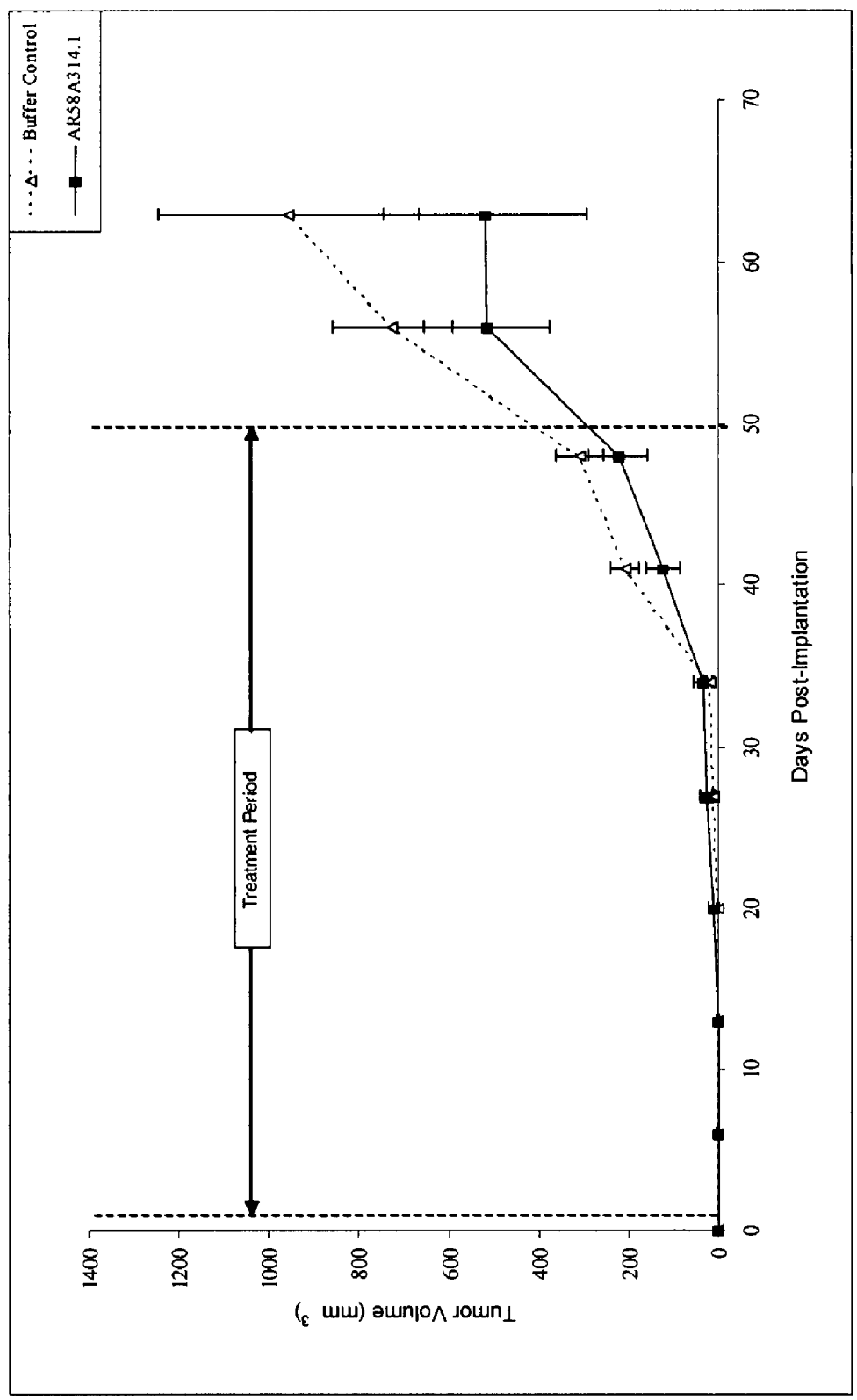
FIG. 6 demonstrates the effect of AR58A314.1 on tumor growth in a prophylactic BxPC-3 pancreatic cancer model. The vertical dashed lines indicate the period during which the antibody was administered. Data points represent the mean +/− SEM.

Examples 1 and 2 demonstrated that AR58A314.1 had anti-cancer properties against human cancer cell lines with detectable binding against several different cancer indications With reference to FIGS. 4 and 5, 4 to 6 week old female SCID mice were implanted with 1 million human lung cancer cells (A549) in 100 microliters saline injected subcutaneously in the scruff of the neck. The mice were randomly divided into 2 treatment groups of 5. On the day after implantation, 20 mg/kg of AR58A314.1 test antibody or buffer control was administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the duration of the study in the same fashion. Tumor growth was measured about every seventh day with calipers. The study was completed after 7 injections (48 days), as the animals reached CCAC end-points due to large ulcerated lesions. Body weights of the animals were recorded once per week for the duration of the study. At the end of the study all animals were euthanized according to CCAC guidelines.

AR58A314.1 reduced tumor growth in the highly aggressive A549 in vivo prophylactic model of human lung cancer.

On day 48 post-implantation, 5 days after the last treatment dose, the mean tumor volume in the AR58A314.1 treated group was 48.6 percent less than that of the buffer control-treated group (FIG. 4). This result did not reach significance, since measurements at the final timepoint were influenced by the loss of mice due to ulcerated lesions before the termination of the study.

There were no clinical signs of toxicity throughout the study. Body weight measured at weekly intervals was a surrogate for well-being and failure to thrive. As seen in FIG. 5, there were no significant differences in the body weights of the control or AR58A314.1-treated groups over the course of the study. There was also no difference in body weight between the two groups at the end of the treatment period (p=0.829, t-test).

Therefore AR58A314.1 was well-tolerated and decreased the tumor burden in this human lung cancer xenograft model.

EXAMPLE 4

In Vivo Tumor Experiments with BxPC-3 Cells

Example 3 demonstrated that AR58A314.1 had anti-cancer properties against a human lung cancer cell line. To determine the efficacy of AR58A314.1 against a human pancreatic cell line, the antibody was tested on a xenograft model of BxPC-3 human pancreatic cancer. With reference to FIGS. 6 and 7, 4 to 6 week old female SCID mice were implanted with 5 million human pancreatic cancer cells (BxPC-3) in 100 microliters saline injected subcutaneously in the scruff of the neck. The mice were randomly divided into 2 treatment groups of 5. On the day after implantation, 20 mg/kg of AR58A314.1 test antibody or buffer control was administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the duration of the study, a total of 8 doses, in the same fashion. Tumor growth was measured about every seventh day with calipers. Body weights of the animals were recorded once per week for the duration of the study. At the end of the study all animals were euthanized according to CCAC guidelines.

Treatment with AR58A314.1 resulted in tumor growth inhibition in the BxPC-3 in vivo prophylactic model of human pancreatic cancer. On day 56 post-implantation, 6 days after the last treatment dose, the mean tumor volume in the AR58A314.1 treated group was 29 percent lower than the tumor volume in the buffer control-treated group (FIG. 6). During the post-treatment follow-up period (day 63), the tumor growth inhibition induced by AR58A314.1 treatment increased to 45.8 percent. These results did not reach significance due to the variability observed between mice within each group.

Figure 7:
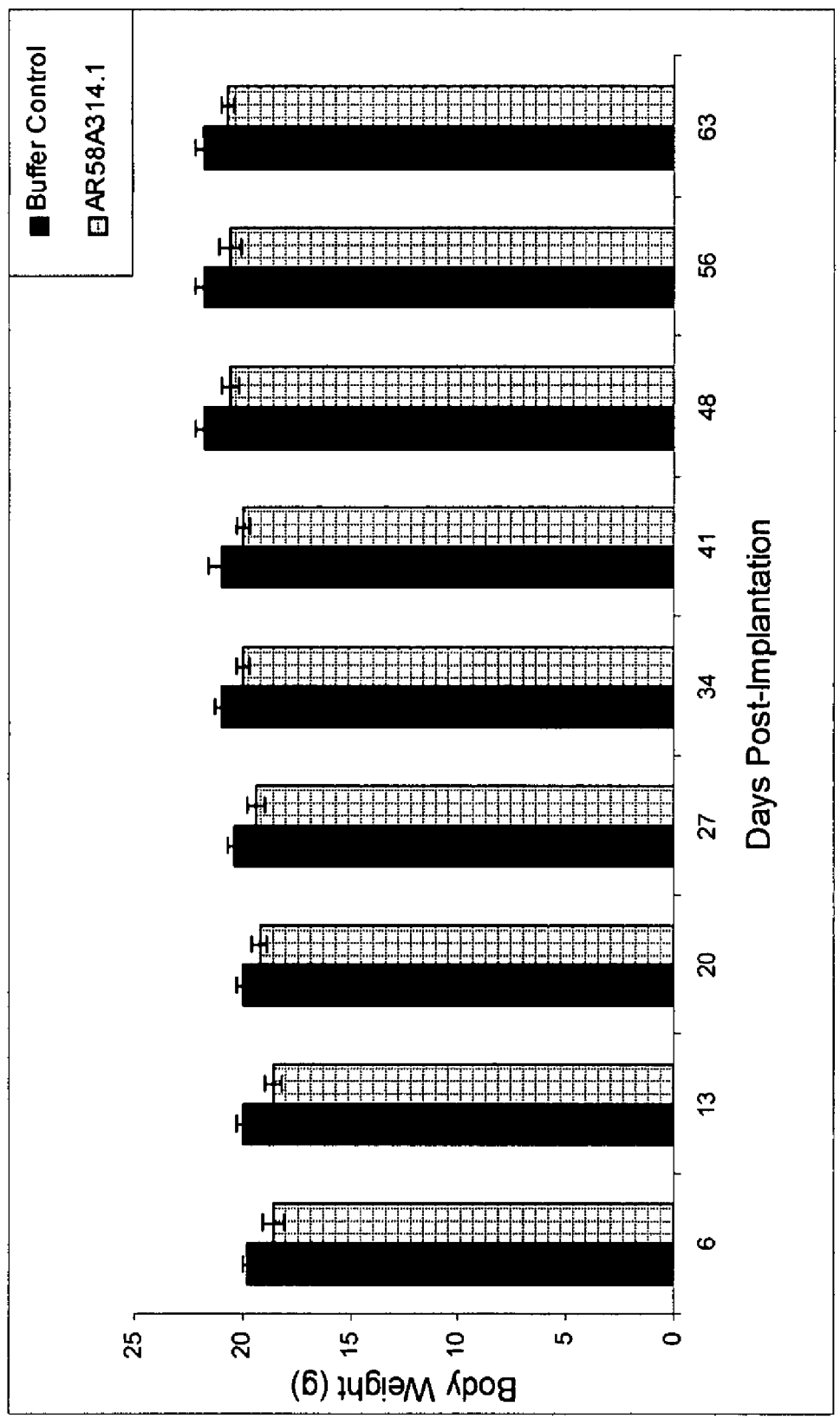
FIG. 7 demonstrates the effect of AR58A314.1 on body weight in a prophylactic BxPC-3 pancreatic cancer model. Data points represent the mean +/− SEM.
Figure 11:
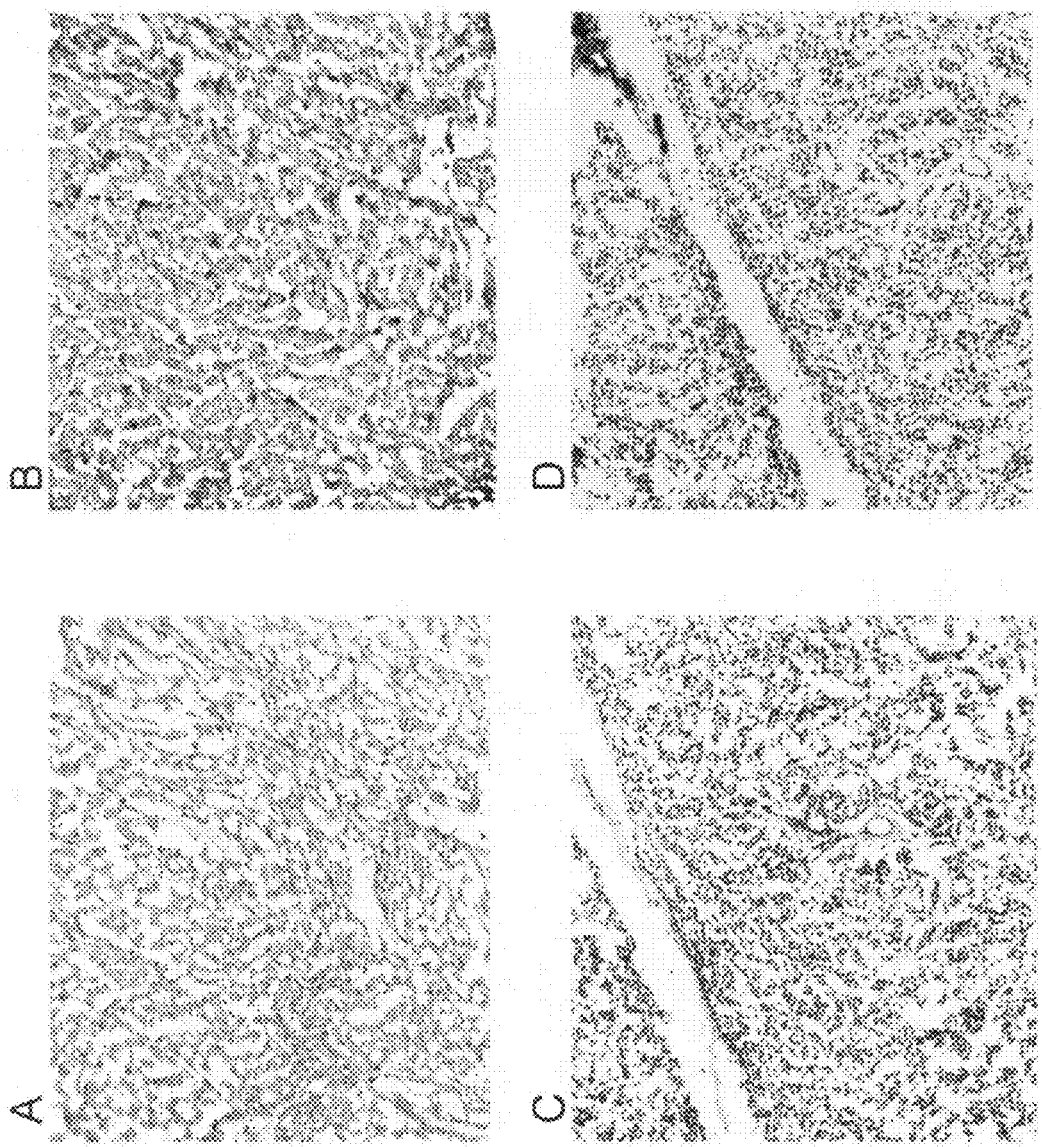
FIG. 11. Representative micrographs showing the binding pattern on normal heart tissue obtained with AR58A314.1 (A) or the positive control antibody (B) and on normal pancreas tissue obtained with AR58A314.1 (C) or the positive control antibody (D) from a normal human tissue microarray. AR58A314.1 displayed negative staining for the normal tissue. Magnification is 200×.

There were no clinical signs of toxicity throughout the study. Body weight measured at weekly intervals was a surrogate for well-being and failure to thrive. As seen in FIG. 7, the body weights of the control or AR58A314.1-treated groups did not decrease over the course of the study. There was also no difference in body weight between the two groups at the end of the treatment period (day 48; p=0.059, t-test) or at the end of the post-treatment follow up period. (day 63; p=0.1479, t-test).

Therefore AR58A314.1 was well-tolerated and decreased the tumor burden in this human pancreatic cancer xenograft model. AR58A314.1 has demonstrated efficacy against two different human cancer indications; pancreatic and lung.

Treatment benefits were observed in several well-recognized models of human cancer disease suggesting pharmacologic and pharmaceutical benefits of this antibody for therapy in other mammals, including man.

EXAMPLE 5

Human Normal and Multi-Tumor Tissue Staining

IHC studies were conducted to characterize the AR58A314.1 antigen distribution in humans. Slides were postfixed for 10 minutes in cold (−20° C.) acetone and then allowed to come to room temperature. Binding of antibodies to 4 human normal tissues (colon, lung, prostate and breast) and 16 human tumor tissues (4 of colon, lung, prostate and breast) was performed using a human, normal and tumor organ tissue, screening array (Tri Star, Rockville, Md.).

Slides were rinsed in 4° C. cold phosphate buffered saline (PBS) 3 times for 2 minutes each followed by blocking endogenous peroxidase activity with washing in 3 percent hydrogen peroxide for 10 minutes. Slides were then rinsed in PBS 3 times for 5 minutes followed by incubation in Universal blocking solution (Dako, Toronto, Ontario) for 5 minutes at room temperature. AR58A314.1, anti-human muscle actin (Clone HHF35, Dako, Toronto, Ontario) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 micrograms/mL for each antibody except for anti-actin which was 0.5 micrograms/mL) and incubated overnight for 1 hour at room temperature. The slides were washed with PBS 3 times for 2 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehydrated with graded ethanols (75-100 percent) and cleared with xylene. Using mounting media (Dako Faramount, Toronto, Ontario) the slides were cover-slipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a histopathologist.

FIG. 8 presents a summary of the results of AR58A314.1 staining of an array of human normal and tumor tissues. The AR58A314.1 antibody showed binding to ¼ of colon and ⅔ of lung (FIG. 9) cancers with no binding to any of the tested normal tissues. These results are consistent with the FACS binding data (FIGS. 2 and 3), which also demonstrate specific binding of this antibody to cancer cells compared to normal cells. AR58A314.1 binding was restricted to tumor cells within the tissue section, and cellular localization was cytoplasmic and membranous. These results suggest that AR58A314.1 is expressed on several different tumor types. In addition, the antigen for AR58A314.1 is not widely expressed on normal tissues, suggesting that the antibody binds specifically to a limited number of tissues in humans.

EXAMPLE 6

Human Normal Tissue Staining

Expanded IHC studies on human normal tissues to evaluate the AR58A314.1 antigen distribution in humans. Binding of antibodies to 20 human normal tissues (adrenal, ovary, pancreas, thyroid, brain (cerebrum), brain (cerebellum), lung, spleen, uterus, cervix, breast, placenta, heart, skin, skeletal muscle, kidney, stomach, small intestine, liver, and salivary gland) was performed using a human, normal tissue micro array (Biochain, CA, USA).

The IHC method used, antibody concentration and isotype controls were the same as mentioned in Example 5 except for anti-actin (concentration of 2 micrograms/mL was used). Slides were microscopically examined using an Axiovert 200 (Zeiss Canada, Toronto, ON) and digital images acquired and stored using Northern Eclipse Imaging Software (Mississauga, ON). Results were read, scored and interpreted by a histopathologist.

FIG. 10 presents a summary of the results of AR58A314.1 staining of an array of human normal tissues. The AR58A314.1 antibody showed no binding to any of the tested tissues (FIG. 1). Eight out of the twenty tissue samples were not scored because of background staining observed in the negative isotype control. The positive antibody control, anti-actin, showed the expected binding to muscular tissues.

AR58A314.1 showed no binding to the tested human normal tissues, this is consistent with the observation in the example above and further demonstrates the differential expression of the epitope targeted by that antibody in tumor versus normal tissues.

EXAMPLE 7

Isolation of Competitive Binders

Given an antibody, an individual ordinarily skilled in the art can generate a competitively inhibiting CDMAB, for example a competing antibody, which is one that recognizes thejsame epitope (Belanger L et al. *Clinica Chimica Acta* 48:15-18 (1973)). One method entails immunizing with an immunogen that expresses the antigen recognized by the antibody. The sample may include but is not limited to tissues, isolated protein(s) or cell line(s). Resulting hybridomas could be screened using a competition assay, which is one that identifies antibodies that inhibit the binding of the test antibody, such as ELISA, FACS or Western blotting. Another method could make use of phage display antibody libraries and panning for antibodies that recognize at least one epitope of said antigen (Rubinstein J L et al. *Anal Biochem* 314:294-300 (2003)). In either case, antibodies are selected based on their ability to displace the binding of the original labeled antibody to at least one epitope of its target antigen. Such antibodies would therefore possess the characteristic of recognizing at least one epitope of the antigen as the original antibody.

EXAMPLE 8

Cloning of the Variable Regions of the AR58A314.1 Monoclonal Antibody

The sequences of the variable regions from the heavy ($V_H$) and light ($V_L$) chains of monoclonal antibody produced by the AR58A314.1 hybridoma cell line can be determined. RNA encoding the heavy and light chains of immunoglobulin can be extracted from the subject hybridoma using standard methods involving cellular solubilization with guanidinium isothiocyanate (Chirgwin et al. Biochem. 18:5294-5299 (1979)). The mRNA can be used to prepare cDNA for subsequent isolation of $V_H$ and $V_L$ genes by PCR methodology known in the art (Sambrook et al., eds., Molecular Cloning, Chapter 14, Cold Spring Harbor laboratories Press, N.Y. (1989)). The N-terminal amino acid sequence of the heavy and light chains can be independently determined by automated Edman sequencing. Further stretches of the CDRs and flanking FRs can also be determined by amino acid sequencing of the $V_H$ and $V_L$ fragments. Synthetic primers can be then designed for isolation of the $V_H$ and $V_L$ genes from AR58A314.1 monoclonal antibody, and the isolated gene can be ligated into an appropriate vector for sequencing. To generate chimeric and humanized IgG, the variable light and variable heavy domains can be subcloned into an appropriate vector for expression.

In another embodiment, AR58A314.1 or its de-immunized, chimeric or humanized version is produced by expressing a nucleic acid encoding the antibody in a transgenic animal, such that the antibody is expressed and can be recovered. For example, the antibody can be expressed in a tissue specific manner that facilitates recovery and purification. In one such embodiment, an antibody of the invention is expressed in the mammary gland for secretion during lactation. Transgenic animals include but are not limited to mice, goat and rabbit.

(i) Monoclonal Antibody

DNA encoding the monoclonal antibody (as outlined in Example 1) is readily isolated and sequenced using conventional procedures (e.g., by using oligonucleotide probes that are capable of binding specifically to genes encoding the heavy and light chains of the monoclonal antibodies). The hybridoma cell serves as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences. Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

(ii) Humanized Antibody

A humanized antibody has one or more amino acid residues introduced into it from a non-human source. These non-human amino acid residues are often referred to as "import" residues, which are typically taken from an "import" variable domain. Humanization can be performed the method of Winter and co-workers by substituting rodent CDRs or CDR sequences for the corresponding sequences of a human antibody (Jones et al., Nature 321:522-525 (1986); Riechmann et al., Nature 332:323-327 (1988); Verhoeyen et al., Science 239:1534-1536 (1988); reviewed in Clark, Immunol. Today 21:397-402 (2000)).

A humanized antibody can be prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

(iii) Antibody Fragments

Various techniques have been developed for the production of antibody fragments. These fragments can be produced by recombinant host cells (reviewed in Hudson, Curr. Opin. Immunol. 11:548-557 (1999); Little et al., Immunol. Today 21:364-370 (2000)). For example, Fab'-SH fragments can be directly recovered from $E.\ coli$ and chemically coupled to form $F(ab')_2$ fragments (Carter et al., Biotechnology 10:163-167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture.

EXAMPLE 9

A Composition Comprising the Antibody of the Present Invention

The antibody of the present invention can be used as a composition for preventing/treating cancer. The composition for preventing/treating cancer, which comprises the antibody of the present invention, are low-toxic and can be administered as they are in the form of liquid preparations, or as pharmaceutical compositions of suitable preparations to human or mammals (e.g., rats, rabbits, sheep, swine, bovine, feline, canine, simian, etc.) orally or parenterally (e.g., intravascularly, intraperitoneally, subcutaneously, etc.). The antibody of the present invention may be administered in itself, or may be administered as an appropriate composition. The composition used for the administration may contain a pharmacologically acceptable carrier with the antibody of the present invention or its salt, a diluent or excipient. Such a composition is provided in the form of pharmaceutical preparations suitable for oral or parenteral administration.

Examples of the composition for parenteral administration are injectable preparations, suppositories, etc. The injectable preparations may include dosage forms such as intravenous, subcutaneous, intracutaneous and intramuscular injections, drip infusions, intraarticular injections, etc. These injectable preparations may be prepared by methods publicly known. For example, the injectable preparations may be prepared by dissolving, suspending or emulsifying the antibody of the present invention or its salt in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant (e.g., polysorbate 80, HCO-50 (polyoxyethylene (50 mols) adduct of hydrogenated castor oil)), etc. As the oily medium, there are employed, e.g., sesame oil, soybean oil, etc., which may be used in combination with a solubilizing agent such as benzyl benzoate, benzyl alcohol, etc. The injection thus prepared is usually filled in an appropriate ampoule. The suppository used for rectal administration may be prepared by blending the antibody of the present invention or its salt with conventional bases for suppositories. The composition for oral administration includes solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and may contain a vehicle, a diluent or excipient conventionally used in the field of pharmaceutical preparations. Examples of the vehicle or excipient for tablets are lactose, starch, sucrose, magnesium stearate, etc.

Advantageously, the compositions for oral or parenteral use described above are prepared into pharmaceutical preparations with a unit dose suited to fit a dose of the active ingredients. Such unit dose preparations include, for example, tablets, pills, capsules, injections (ampoules), suppositories, etc. The amount of the aforesaid compound contained is generally 5 to 500 mg per dosage unit form; it is preferred that the antibody described above is contained in about 5 to about 100 mg especially in the form of injection, and in 10 to 250 mg for the other forms.

The dose of the aforesaid prophylactic/therapeutic agent or regulator comprising the antibody of the present invention may vary depending upon subject to be administered, target disease, conditions, route of administration, etc. For example, when used for the purpose of treating/preventing, e.g., breast cancer in an adult, it is advantageous to administer the antibody of the present invention intravenously in a dose of about 0.01 to about 20 mg/kg body weight, preferably about 0.1 to about 10 mg/kg body weight and more preferably about 0.1 to about 5 mg/kg body weight, about 1 to 5 times/day, preferably about 1 to 3 times/day. In other parenteral and oral administration, the agent can be administered in a dose corresponding to the dose given above. When the condition is especially severe, the dose may be increased according to the condition.

The antibody of the present invention may be administered as it stands or in the form of an appropriate composition. The composition used for the administration may contain a pharmacologically acceptable carrier with the aforesaid antibody or its salts, a diluent or excipient. Such a composition is provided in the form of pharmaceutical preparations suitable for oral or parenteral administration (e.g., intravascular injection, subcutaneous injection, etc.). Each composition described above may further contain other active ingredients. Furthermore, the antibody of the present invention may be used in combination with other drugs, for example, alkylating agents (e.g., cyclophosphamide, ifosfamide, etc.), metabolic antagonists (e.g., methotrexate, 5-fluorouracil, etc.), anti-tumor antibiotics (e.g., mitomycin, adriamycin, etc.), plant-derived anti-tumor agents (e.g., vincristine, vindesine, Taxol, etc.), cisplatin, carboplatin, etoposide, irinotecan, etc. The antibody of the present invention and the drugs described above may be administered simultaneously or at staggered times to the patient.

The method of treatment described herein, particularly for cancers, may also be carried out with administration of other antibodies or chemotherapeutic agents. For example, an antibody against EGFR, such as ERBITUX® (cetuximab), may also be administered, particularly when treating colon cancer. ERBITUX® has also been shown to be effective for treatment of psoriasis. Other antibodies for combination use include Herceptin® (trastuzumab) particularly when treating breast cancer, AVASTIN® particularly when treating colon cancer and SGN-15 particularly when treating non-small cell lung cancer. The administration of the antibody of the present invention with other antibodies/chemotherapeutic agents may occur simultaneously, or separately, via the same or different route.

The chemotherapeutic agent/other antibody regimens utilized include any regimen believed to be optimally suitable for the treatment of the patient's condition. Different malignancies can require use of specific anti-tumor antibodies and specific chemotherapeutic agents, which will be determined on a patient to patient basis. In a preferred embodiment of the invention, chemotherapy is administered concurrently with or, more preferably, subsequent to antibody therapy. It should be emphasized, however, that the present invention is not limited to any particular method or route of administration.

The preponderance of evidence shows that AR58A314.1 mediates anti-cancer effects through ligation of an epitope present on cancer cell lines and human tumor tissue. Further it could be shown that the AR58A314.1 antibody could be used in detection of cells and/or tissues which express the epitope which specifically binds thereto, utilizing techniques illustrated by, but not limited to FACS, cell ELISA or IHC.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. The isolated monoclonal antibody produced by the hybridoma deposited with the IDAC as accession number 141205-02.

2. An antigen binding fragment of the isolated monoclonal antibody of claim 1.

3. A humanized version of the isolated monoclonal antibody produced by the hybridoma deposited with the IDAC as accession number 141205-02 or an antigen binding fragment produced from said humanized antibody.

4. An antigen binding fragment of the humanized antibody of claim 3.

5. A chimeric version of the isolated monoclonal antibody produced by the hybridoma deposited with the IDAC as accession number 141205-02or an antigen binding fragment produced from said chimeric antibody.

6. An antigen binding fragment of the chimeric antibody of claim 5.

7. The isolated antibody or an antigen binding fragment thereof, of any one off claims 1, 2, 3, 4, 5 or 6 conjugated with a member selected from the group consisting of cytotoxic moieties, enzymes, radioactive compounds, cytokines, interferons, target or reporter moieties and hematogenous cells.

8. The isolated hybridoma cell line deposited with the IDAC as accession number 141205-02.

9. A method for initiating cellular cytotoxicity of cancerous cells in a tissue sample selected from a human lung, pancreatic, ovarian or colon tumor comprising:
providing a tissue sample from said human lung, pancreatic, ovarian or colon tumor;
providing the isolated monoclonal antibody produced by the hybridoma deposited with the IDAC as accession number 141205-02, the humanized antibody of the isolated monoclonal antibody produced by the hybridoma deposited with the IDAC as accession fluter 141205-02, the chimeric antibody of the isolated monocional antibody produced by the hybridorna deposited with the IDAC as accession number 141205-02, or an antigen binding fragment thereof, which antigen binding fragment is characterized by an ability to competitively inhibit binding of said isolated monoclonal antibody to its target antigen; and
contacting said isolated ruonocional antibody, said humanized antibody, said chimeric antibody or antigen binding fragment thereof with said tissue sample;
wherein binding of said isolated monoclonal antibody, said humanized antibody, said chimeric antibody or antigen binding fragment thereof with said tissue sample induces cytotoxicity.

10. A method of reduction of a human lung, pancreatic, ovarian or colon tumor susceptible to cellular cytotoxicity in a mammal, wherein said human tumor expresses at least one epitope of an antigen which specifically binds to the isolated monoclonal antibody produced by the hybridoma deposited with the IDAC as accession number 141205-02 or an antigen binding fragment thereof, which antigen binding fragment is characterized by an ability to competitively inhibit binding of said isolated monoclonal antibody to its target antigen, comprising administering to said mammal said monoclonal antibody or said antigen binding fragment thereof in an amount effective to result in a reduction of said mammal's lung, pancreatic, ovarian or colon tumor burden.

11. The method of claim 10 wherein said isolated monoclonal antibody is conjugated to a cytotoxic moiety.

12. The method of claim 11 wherein said cytotoxic moiety is a radioactive isotope.

13. The method of claim 10 wherein said isolated monoclonal antibody or antigen binding fragment thereof activates complement.

14. The method of claim 10 wherein said isolated monoclonal antibody or antigen biding fragment thereof mediates antibody dependent cellular cytotoxicity.

15. The method of claim 10 wherein said isolated monoclonal antibody is a humanized version of the isolated monoclonal antibody produced by the hybridoma deposited with the IDAC as accession number 141205-02 or an antigen binding fragment produced from said humanized antibody.

16. The method of claim 10 wherein said isolated monoclonal antibody is a chimeric version of the isolated monoclonal antibody produced by the hybridoma deposited with the IDAC as accession number 141205-02 or an antigen binding fragment produced from said chimeric antibody.

17. A monoclonal antibody which specifically binds to the same epitope or epitopes as the isolated monoclonal antibody produced by the hybridoma deposited with the IDAC as accession number 141205-02.

18. A method of reduction of a human lung, pancreatic, ovarian or colon tumor in a mammal, wherein said human lung, pancreatic, ovarian or colon tumor expresses at least one epitope of an antigen which specifically binds to the isolated monoclonal antibody produced by the hybridoma deposited with the IDAC as accession number 141205-02 or an antigen binding fragment thereof, which antigen binding fragment is characterized by an ability to competitively inhibit binding of said isolated monoclonal antibody to its target antigen, comprising administering to said mammal said monoclonal antibody or antigen binding fragment thereof in an amount effective to result in a reduction of said mammal's lung, pancreatic, ovarian or colon tumor burden.

19. The method of claim 18 wherein said isolated monoclonal antibody is conjugated to a cytotoxic moiety.

20. The method of claim 19 wherein said cytotoxic moiety is a radioactive isotope.

21. The method of claim 18 wherein said isolated monoclonal antibody or antigen binding fragment thereof activates complement.

22. The method of claim 18 wherein said isolated monoclonal antibody or antigen binding fragment thereof mediates antibody dependent cellular cytotoxicity.

23. The method of claim 18 wherein said isolated monoclonal antibody is a humanized antibody of the isolated monoclonal antibody produced by the hybridoma deposited with the IDAC as accession number 141205-02 or an antigen binding fragment produced from said humanized antibody.

24. The method of claim 18 wherein said isolated monoclonal antibody is a chimeric version of the isolated monoclonal antibody produced by the hybridoma deposited with the IDAC as accession number 141205-02 or an antigen binding fragment produced from said chimeric antibody.

25. A method of reduction of a human lung, pancreatic, ovarian or colon tumor in a mammal, wherein said human lung, pancreatic, ovarian or colon tumor expresses at least one epitope of an antigen which specifically binds to the isolated monoclonal antibody produced by the hybridoma deposited with the IDAC as accession number 141205-02 or an antigen binding fragment thereof, which antigen binding fragment is characterized by an ability to competitively inhibit binding of said isolated monoclonal antibody to its target antigen, comprising administering to said mammal said monoclonal antibody or antigen binding fragment thereof in conjunction with at least one chemotherapeutic agent in an amount effective to result in a reduction of said mammal's lung, pancreatic, ovarian or colon tumor burden.

26. The method of claim 25 wherein said isolated monoclonal antibody is conjugated to a cytotoxic moiety.

27. The method of claim 26 wherein said cytotoxic moiety is a radioactive isotope.

28. The method of claim 25 wherein said isolated monoclonal antibody or antigen binding fragment thereof activates complement.

29. The method of claim 25 wherein said isolated monoclonal antibody or antigen binding fragment thereof mediates antibody dependent cellular cytotoxicity.

30. The method of claim 25 wherein said isolated monoclonal antibody is a humanized version of the isolated monoclonal antibody produced by the hybridoma deposited with the IDAC as accession number 141205-02 or an antigen binding fragment produced from said humanized antibody.

31. The method of claim 25 wherein said isolated monoclonal antibody is a chimeric version of the isolated monoclonal antibody produced by the hybridoma deposited with the IDAC as accession number 141205-02 or an antigen binding fragment produced from said chimeric antibody.

32. A binding assay to determine a presence of cancerous cells in a tissue sample selected from a human tumor, which is specifically bound by the isolated monoclonal antibody produced by hybridoma cell line AR58A314.1 having IDAC Accession No. 141205-02, the humanized version of the isolated monoclonal antibody produced by the hybridoma deposited with the IDAC as accession number 141205-02 or the chimeric version of the isolated monoclonal antibody produced by the hybridoma deposited with the IDAC as accession number 141205-02, or an antigen binding fragment thereof, comprising:
    providing a tissue sample from said human tumor;
    providing at least one of said isolated monoclonal antibody, said humanized antibody, said chimeric antibody or said antigen binding fragment thereof that recognizes the same epitope or epitopes as those recognized by the isolated monoclonal antibody produced by a hybridoma cell line AR58A314.1 having IDAC Accession No. 141205-02;
    contacting at least one of said provided antibodies or antigen binding fragments thereof with said tissue sample; and
    determining binding of said at least one provided antibody or antigen binding fragment thereof with said tissue sample;
    whereby the presence of said cancerous cells in said tissue sample is indicated.

33. A composition effective for treating a human cancerous tumor comprising in combination:
    an antibody or antigen binding fragment of any one of claims 1,2,3,4,5,6, or 17;
    a conjugate of said antibody or an antigen binding fragment thereof with a member selected from the group consisting of cytotoxic moieties, enzymes, radioactive compounds, cytokines, interferons, target or reporter moieties and hematogenous cells; and
    a requisite amount of a pharmacologically acceptable carrier;
    wherein said composition is effective for treating said human cancerous tumor.

34. A composition effective for treating a human cancerous tumor comprising in combination:
    an antibody or antigen binding fragment of any one of claims 1,2,3,4,5,6, or 17; and
    a requisite amount of a pharmacologically acceptable carrier;
    wherein said composition is effective for treating said human cancerous tumor.

35. A composition effective for treating a human cancerous tumor comprising in combination:
    a conjugate of an antibody, or antigen binding fragment of any one of claims 1,2,3,4,5,6, or 17; with a member selected from the group consisting of cytotoxic moieties, enzymes, radioactive compounds, cytokines, interferons, target or reporter moieties and hematogenous cells; and
    a requisite amount of a pharmacologically acceptable carrier;
    wherein said composition is effective for treating said human cancerous tumor.

36. An assay kit for detecting the presence of a human cancerous tumor, wherein said human cancerous tumor expresses at least one epitope of an antigen which specifically binds to the isolated monoclonal antibody produced by the hybridoma deposited with the IDAC as accession number 141205-02 or an antigen binding fragment thereof, which antigen binding fragment is characterized by an ability to competitively inhibit binding of said isolated monoclonal antibody to its target antigen, the kit comprising the isolated monoclonal antibody produced by the hybridoma deposited with the IDAC as accession number 141205-02 or an antigen binding fragment thereof, and means for detecting whether the monoclonal antibody, or antigen binding fragment thereof, is bound to a polypeptide whose presence, at a particular cut-off level, is diagnostic of said presence of said human cancerous tumor.

* * * * *